US009204858B2

(12) United States Patent
Pelissier et al.

(10) Patent No.: US 9,204,858 B2
(45) Date of Patent: Dec. 8, 2015

(54) ULTRASOUND PULSE-WAVE DOPPLER MEASUREMENT OF BLOOD FLOW VELOCITY AND/OR TURBULENCE

(75) Inventors: Laurent Pelissier, North Vancouver (CA); Kris Dickie, Vancouver (CA); Bo Zhuang, New Westminster (CA)

(73) Assignee: Ultrasonix Medical Corporation, British Columbia (CA)

(*) Notice: Subject to any disclaimer, the term of this patent is extended or adjusted under 35 U.S.C. 154(b) by 832 days.

(21) Appl. No.: 13/021,676

(22) Filed: Feb. 4, 2011

(65) Prior Publication Data

US 2011/0196237 A1 Aug. 11, 2011

Related U.S. Application Data

(60) Provisional application No. 61/302,055, filed on Feb. 5, 2010.

(51) Int. Cl.
| | | |
|---|---|---|
| *A61B 8/00* | (2006.01) | |
| *A61B 8/06* | (2006.01) | |
| *A61B 8/08* | (2006.01) | |
| *G01S 15/89* | (2006.01) | |
| *G01S 7/52* | (2006.01) | |

(52) U.S. Cl.
CPC ... *A61B 8/06* (2013.01); *A61B 8/08* (2013.01); *A61B 8/0891* (2013.01); *A61B 8/463* (2013.01); *A61B 8/466* (2013.01); *A61B 8/467* (2013.01); *A61B 8/488* (2013.01); *A61B 8/543* (2013.01); *G01S 7/52073* (2013.01); *G01S 15/8984* (2013.01)

(58) Field of Classification Search
CPC ........... A61B 8/06; A61B 8/461; A61B 8/488
USPC .......................................................... 600/445
See application file for complete search history.

(56) References Cited

U.S. PATENT DOCUMENTS

| | | | |
|---|---|---|---|
| 4,622,977 A | 11/1986 | Namekawa et al. | |
| 5,271,404 A * | 12/1993 | Corl et al. | 600/454 |
| 5,409,010 A | 4/1995 | Beach et al. | |
| 5,701,898 A | 12/1997 | Adam et al. | |
| 5,724,974 A * | 3/1998 | Goodsell et al. | 600/453 |
| 5,910,119 A * | 6/1999 | Lin | 600/455 |
| 5,912,656 A * | 6/1999 | Tham et al. | 345/418 |
| 6,464,637 B1 * | 10/2002 | Criton et al. | 600/441 |

(Continued)

OTHER PUBLICATIONS

Boote, Evan J., "AAPM/RSNA Physics Tutorial for Residents: Topics in US", RadioGraphics 2003, 23:1315-1327.

*Primary Examiner* — Rajeev Siripurapu
(74) *Attorney, Agent, or Firm* — Anthony M. Del Zoppo, III; Driggs, Hogg, Daugherty & Del Zoppo, Co., LPA

(57) ABSTRACT

Apparatus and methods for measuring and analyzing blood flow in vessels in the bodies of living subjects are provided. The true velocity vector, or a projection thereof onto a scan plane, for blood flowing at a location in a vessel is determined from multiple Doppler velocity components. The true velocity vector is displayed as a directional marker on an image comprising the vessel. The true velocity magnitude and angle, and scalar blood flow characteristics derived therefrom, are plotted as a functions of time and/or position across the depiction of the blood vessel in the image. Time intervals for which blood flow characteristic data is displayed and/or determined may be user configurable.

26 Claims, 16 Drawing Sheets

(56) References Cited

U.S. PATENT DOCUMENTS

| | | | |
|---|---|---|---|
| 2002/0091319 A1* | 7/2002 | Moehring et al. | 600/454 |
| 2004/0254486 A1* | 12/2004 | Heimdal | 600/513 |
| 2006/0052698 A1* | 3/2006 | Loupas | 600/437 |
| 2007/0073153 A1 | 3/2007 | Tortoli | |
| 2008/0259312 A1* | 10/2008 | Carnegie et al. | 356/28 |
| 2009/0003669 A1* | 1/2009 | Parks et al. | 382/128 |
| 2009/0143667 A1* | 6/2009 | Kovacs et al. | 600/410 |

* cited by examiner

ULTRASOUND PULSE-WAVE DOPPLER MEASUREMENT OF BLOOD FLOW VELOCITY AND/OR TURBULENCE

CROSS-REFERENCE TO RELATED APPLICATIONS

This application claims the benefit under 35 U.S.C. §119 of U.S. Patent Application No. 61/302,055 filed on 5 Feb. 2010 and entitled ULTRASOUND PULSE-WAVE DOPPLER MEASUREMENT OF BLOOD FLOW VELOCITY AND/OR TURBULENCE which is hereby incorporated herein by reference.

TECHNICAL FIELD

The present invention relates to medical ultrasound. In particular, the present invention relates to Pulse-Wave (PW) Doppler exams used to measure and analyze blood flow in vessels of living subjects.

BACKGROUND

PW Doppler ultrasound is used in medical ultrasound exams to examine blood flood and measure blood flow velocity. FIG. 1 is a schematic depiction illustrating the application of PW Doppler ultrasound to measure blood flow velocity. A blood vessel 12 contains blood flowing in the direction indicated by arrow 14. An ultrasound probe 16 transmits a series of ultrasound pulses along a scan line 17. Pulses are reflected back to ultrasound probe 16 by structures along scan line 17. Signals reflected from structures at a particular depth may be identified by time-gating the registration of reflected pulses received at probe 16. Transmitted pulses incident on sample volume 18 within blood vessel 12 are reflected by erythrocytes moving in the flowing blood. Because the transmitted pulses interact with moving blood components, such as erythrocytes, the frequency of the reflected pulses will differ from the frequency of the transmitted pulses. This change in frequency is known as a Doppler shift. After determining the frequency of the pulses received from sample volume 18, the velocity of blood flowing through the target volume may be calculated from the frequency shift using the Doppler equation $$V = \frac{F_D c}{2 f_0}$$

where V is the velocity in the sample volume, $F_D$ is the Doppler shift, c is the velocity of sound in blood, and $f_0$ is the transmitted frequency.

Because scan line 17 is at an angle to the direction of the blood flow, the Doppler shift indicates only the component of blood flow velocity parallel to scan line 17. To obtain the true blood flow velocity, the measured velocity value can be angle-corrected for the angle θ between scan line 17 and the direction of blood flow 14. This may be achieved, for example, by dividing the measured velocity value by the cosine of the angle θ between the scan line 17 and the blood flow direction 14.

In conventional ultrasound Doppler exams, angle correction is based on an estimate of the angle between the scan line and the direction of blood flow. Typically, a human sonographer estimates the direction of blood flow from the shape and configuration of anatomical structures on a B-mode image, and manually places a cursor on the image to indicate the blood flow direction. The direction of blood flow is usually assumed to be parallel to the walls of the blood vessel. This method of manual angle estimation may introduce error in velocity measurement since blood flow direction is not necessarily parallel to the blood vessel wall. The error may be enlarged when using a large correction angle (e.g., an angle greater than 60°) since small changes to such a large angle result in a comparatively large difference in the value of the cosine of the angle. To minimize error in manual angle estimation, sonographers must position the ultrasound probe manually to reduce the angle between the ultrasound beam and the blood flow, which is time consuming and requires experience. In some cases, repeated velocity measurements (preferably with different angles) may be made to gain a feel for the variability of measurements. Even with repetitive measurements, the principal blood flow direction may not be found since the haemodynamics of the blood flow may be complex for reasons including helical, converging, diverging and/or turbulent flow patterns; bleeding (blood passing through the vessel wall); atherosclerosis (changes in blood vessel shape); stenosis (narrowing of blood vessels); complex blood vessel geometry; and changing blood flow direction over time.

In addition, when the blood flow direction is perpendicular to the ultrasound beam direction, no Doppler frequency shift will be detected. This is problematic in cases where the sample volume spans a helical flow, in which cases there are Doppler shifts in a wide range of directions. In addition, because of the finite size of the Doppler sample volume, transit time spectral broadening may produce bidirectional Doppler shifts.

Several approaches using ultrasound pulses transmitted and/or received at several different directions, known as vector Doppler measurement, have been proposed to improve the accuracy of the blood flow velocity measurement. Since the Doppler pulses corresponding to each direction can be used to estimate the velocity component along that direction (the bisector of the angle between each transmit direction and corresponding receive direction), an estimate of blood flow velocity in an arbitrary direction can be reconstructed from the components of the velocities along the measured directions. Sample publications describing the principles and implementation of vector Doppler measurement include the following:

U.S. Pat. No. 4,622,977, Namekawa et al.
U.S. Pat. No. 5,701,898, Adam et al.
U.S. Pat. No. 5,724,974, Goodsell, Jr. et al.
U.S. Pat. No. 5,409,010, Beach
U.S. Pat. No. 5,910,119, Lin
U.S. Pat. No. 6,464,637, Criton et al.
U.S. Pat. No. 6,589,179, Criton et al.
US Patent Application no. 2007/0073153, Tortoli Since vector Doppler approaches differ from conventional Doppler ultrasound, implementing these approaches in a manner that is intuitive and easily learned by sonographers is a challenge. A related challenge is presenting results of vector Doppler ultrasound measurements in a way that is readily intelligible and useful for clinical purposes. There is accordingly a need for vector Doppler ultrasound systems that provide improved accuracy of velocity measurement and other haematological measurements, are intuitive and easily learned by sonographers, and provide interfaces that present results of vector Doppler ultrasound measurements in a readily intelligible and clinically useful fashion.

One particular application of Doppler ultrasound is the study of blood flow turbulence, particularly in regions of actual or suspected plaque deposits and/or stenoses. Information about blood flow turbulence may be used to evaluate the risk of blood vessel trauma, such as plaque rupture, which are known to cause stroke and myocardial infarction. Blood flow turbulence has previously been estimated by reconstructing the velocity components perpendicular to the vessel axis, on the assumption that flows perpendicular to the vessel axis indicate turbulence. These methods work well when the vessel wall is parallel to the vessel axis. However, plaque deposits may introduce local variations into the shape of the vessel wall that change flow direction but do not cause turbulent flow. There is accordingly a need for ultrasound Doppler systems that provide a better method for evaluating blood flow turbulence.

The foregoing examples of the related art and limitations related thereto are intended to be illustrative and not exclusive. Other limitations of the related art will become apparent to those of skill in the art upon a reading of the specification and a study of the drawings.

SUMMARY

An aspect of the invention provides a method for displaying blood flow information concerning blood in a vessel, the method comprising producing an ultrasound image of the vessel, obtaining a true velocity vector of blood passing through a sample volume located in the vessel, and displaying a vector-marker corresponding to the true velocity vector on the ultrasound image at a location corresponding to the sample volume. In some embodiments corresponding to this aspect, the method comprises, for each of a plurality of time intervals, obtaining a true velocity vector of blood passing through the sample volume, and displaying a vector-marker corresponding to the true velocity vector on the ultrasound image at a location corresponding to the sample volume. In some embodiments corresponding to this aspect, the method comprises, for each of a plurality of time intervals, for each of a plurality of time intervals, obtaining a true velocity vector of blood passing through the sample volume located in the vessel, determining a scalar blood flow characteristic value based on the true velocity vector, and plotting the scalar blood flow characteristic value on a timescale at a location corresponding to the time interval. In some such embodiments, the scalar blood flow characteristic comprises velocity angle and/or velocity magnitude.

Another aspect of the invention provides a method for displaying blood flow information concerning blood in a vessel, the method comprising, for each of a plurality of sample volumes in the vessel, obtaining a velocity vector for blood passing through the sample volume, determining a scalar blood flow characteristic based on the velocity vector, plotting the scalar blood flow characteristic on a first graph at a location corresponding to the sample volume. In some embodiments corresponding to this aspect, the scalar blood flow characteristic comprises velocity angle and/or velocity magnitude. In some embodiments corresponding to this aspect, the method comprises, for each of the plurality of sample volumes, obtaining a measurement of a strength of ultrasound echoes returned from the sample volume, and determining an instantaneous volumetric rate of blood flow through the sample volume based on the echo strength measurement and velocity magnitude value, and the scalar blood flow characteristic comprises the instantaneous volumetric rate of blood flow. In some embodiments corresponding to this aspect, the method comprises, for each of the plurality of sample volumes and for each of a plurality of time intervals, obtaining a measurement of a strength of ultrasound echoes returned from the sample volume, determining an instantaneous volumetric rate of blood flow through the sample volume for the time interval based on the echo strength measurement and velocity magnitude value, and determining a cumulative blood flow volume through the sample volume based on the instantaneous volumetric rates of blood flow determined for the plurality of time intervals, and the scalar blood flow characteristic comprises cumulative blood flow volume over the plurality of time intervals. In some embodiments corresponding to this aspect, the method comprises, producing an ultrasound image of the vessel, and determining the location of the plurality of sample volumes in the vessel by a correspondence between an elongate user controllable cursor positioned on the image and pixels of the image. In some such embodiments, the step of plotting the scalar blood flow characteristic on the first graph at the location corresponding to the sample volume comprises plotting the scalar blood flow characteristic at a location on the ultrasound image of the vessel corresponding to the sample volume.

A further aspect of the invention provides vector Doppler ultrasound system for displaying blood velocity information for blood inside a body, the system comprising a controller, an ultrasound transducer connected to the controller to provide ultrasound echo signals, a display connected to the controller, the display having a user-positionable cursor, and an input device connected to the controller, in which the controller is configured to generate an image of the body based on ultrasound echo signals from the ultrasound transducer, position the user-positionable cursor on the display according to input from the input device, determine a location of a sample volume in the body according to a correspondence between the position of the user-positionable cursor and the image of the body, obtain a true velocity vector of blood passing through the sample volume located in the vessel, and display a vector-marker corresponding to the true velocity vector on the image at a location corresponding to the sample volume.

Yet another aspect of the invention provides a vector Doppler ultrasound system for displaying blood velocity information for blood inside a body, the system comprising a controller, an ultrasound transducer connected to the controller to provide ultrasound echo signals, a display connected to the controller, the display having a user-positionable cursor, and an input device connected to the controller, in which the controller is configured to generate an image of the body based on ultrasound echo signals from the ultrasound transducer, position the user-positionable cursor on the display according to input from the input device, determine a location of a sample volume in the body according to a correspondence between the position of the user-positionable cursor and the image of the body, generate a true velocity vector of blood passing through the sample volume located in the vessel based on ultrasound echo signals from the ultrasound transducer, determine a scalar blood flow characteristic based on the true velocity vector; and display the scalar blood flow characteristic on the display.

Further aspects of the invention and features of example embodiments are described below.

BRIEF DESCRIPTION OF DRAWINGS

Example embodiments are illustrated in the appended drawings. The embodiments and figures disclosed herein are illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
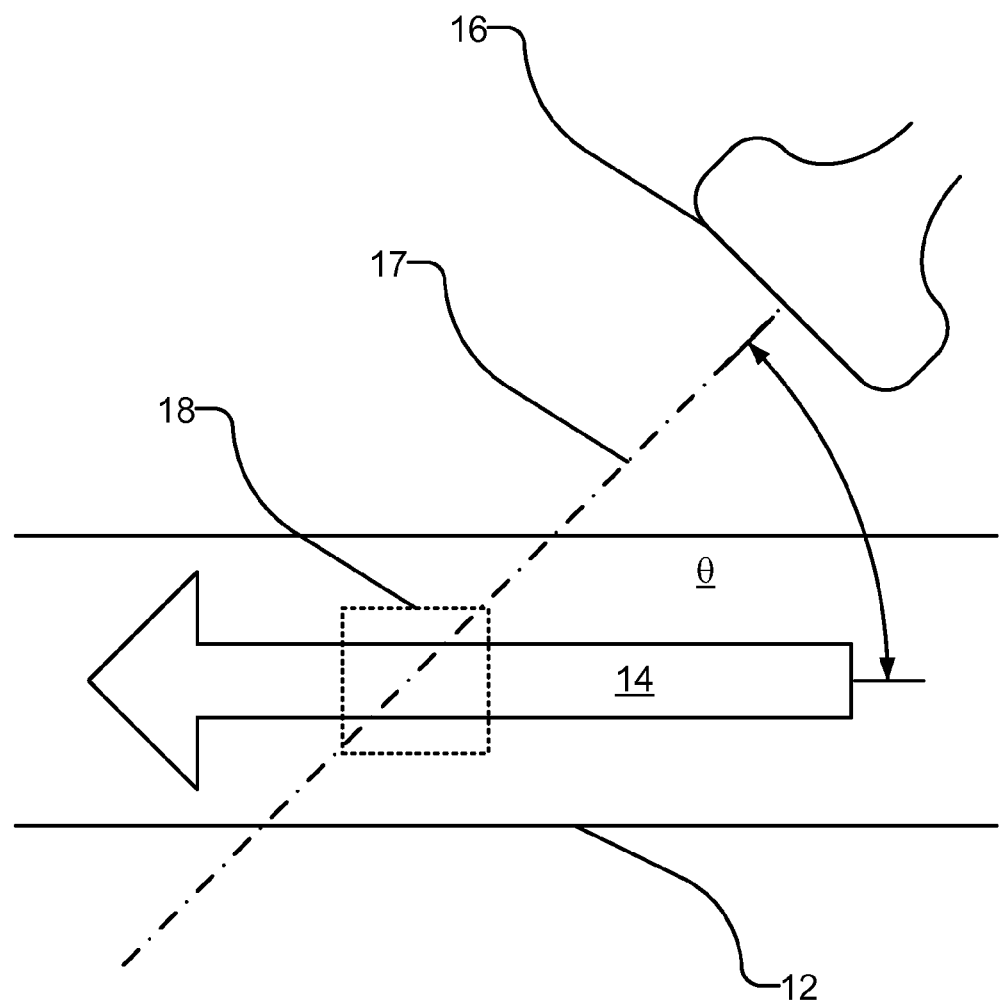
FIG. 1 is a schematic elevation view of a conventional Doppler ultrasound system used in the measurement of blood flow characteristics.
Figure 2:
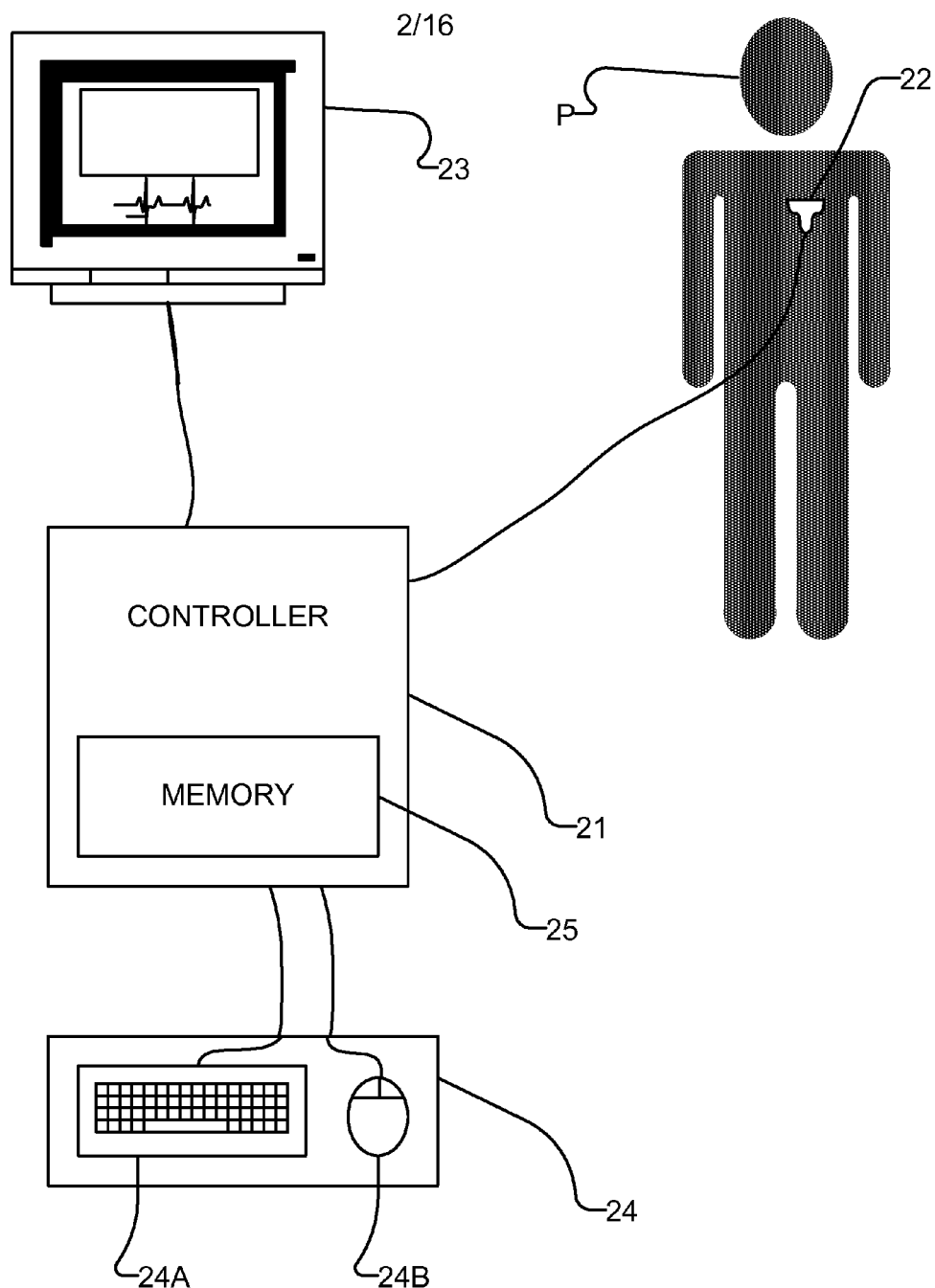
FIG. 2 is a schematic view of a vector Doppler ultrasound system.

FIG. 2 shows a vector Doppler ultrasound system 20 according to an example embodiment. System 20 comprises a controller 21 connected to an ultrasound transducer 22, a display 23, and a user input device 24. Transducer 22 may comprise, for example, a transducer from a commercially available ultrasound system.

Ultrasound transducer 22 emits ultrasound pulses into the body of patient P. Ultrasound pulses emitted by transducer 22 are reflected off of structures in the body of patient P. Transducer 21 receives reflected ultrasound pulses that return in its direction. Controller 21 may be configured to control aspects of the operation of ultrasound transducer 22. For example, controller 21 may control the transmission of pulses from ultrasound transducer 22 and/or the gating of samples of reflected pulses received at ultrasound transducer 22.

Controller 21 comprises a memory 25. In some embodiments, memory 25 may be external to controller 21. Controller 21 may be configured to store data representative of signals acquired by transducer 22 in memory 25. Controller 21 processes the ultrasound data acquired from ultrasound transducer 22. Controller 21 is configured to process the ultrasound data to generate vector Doppler information and B-mode images. Particular example methods for generating vector Doppler information are described elsewhere herein.

Vector Doppler information generated by controller 21 may comprise measurements and/or estimates of blood velocity characteristics, such as velocity magnitude and velocity angle. Controller 21 may be configured to compute derivative blood velocity information. For example, controller 21 may be configured to compute one or more mathematical functions of blood velocity characteristics, time-averages of blood velocity characteristics, or the like. Some other example types of blood velocity information that may be generated by controller 21 are set out below.

Controller 21 may be configured to store vector Doppler information and B-mode image data in memory 25. Controller 22 may be configured to store generated vector Doppler information in data structures which associate generated vector Doppler information with the time and/or sample volumes in the body of patient P to which the information pertains. In some embodiments, controller 22 is configured to store vector Doppler information in memory 25 in data structures that indicate, implicitly or explicitly, the order in which the vector Doppler information was generated.

Controller 21 is configured to display B-mode images generated from ultrasound data on display 23. Controller 21 is configured to display vector Doppler information in graphical and/or numerical formats on display 23. In some embodiments, controller 21 displays vector Doppler information overlaid on B-mode images. Particular example displays of vector Doppler information are described elsewhere herein. Controller 21 may be configured to generate and store display-formatted vector Doppler information and/or B-mode image data in data structures suitable for use by a display controller (not shown) to display such information and/or images on display 23.

Input device 24 provides user input to controller 21. In the illustrated embodiment, input device 24 comprises keyboard 24A and computer mouse 24B. Input device 24 may comprise other user interfaces. In some embodiments, display 23 comprises a touch screen, which may form part of input device 24.

A user may use input device 24 to control aspects of the operation of controller 21. Input device 24 may provide controls for manipulating the B-mode images generated by controller 21. For example, a user may interact with input device 24 to control the gating of samples received at ultrasound transducer 22 and thereby change the B-mode image displayed by controller 21 on display 23. Control may be provided for other aspects of controller 21, such as steering the beam of ultrasound emitted by ultrasound transducer 22. Transmit and receive focusing and steering of ultrasound pulses may be achieved through dynamic delay line control of the transmit and receive elements of transducer 22.

Input device 24 may provide controls for controlling aspects of the generation of vector Doppler information and/or B-mode images. For example, user input provided via input device 24 may control controller 21 to generate blood velocity measurements for particular sample volumes in patient P. Other examples of aspects of the generation of vector Doppler information and/or B-mode images that may be controlled by controls on input device 24 are described herein.

Input device 24 may provide controls for controlling aspects of the display of vector Doppler information and/or B-mode images on display 23. For example, user input provided via input device 24 may control the selection and arrangement of vector Doppler information on display 23. Other examples of aspects of the display of vector Doppler information and/or B-mode images that may be controlled by controls on input device 24 are described herein.

Figure 3:
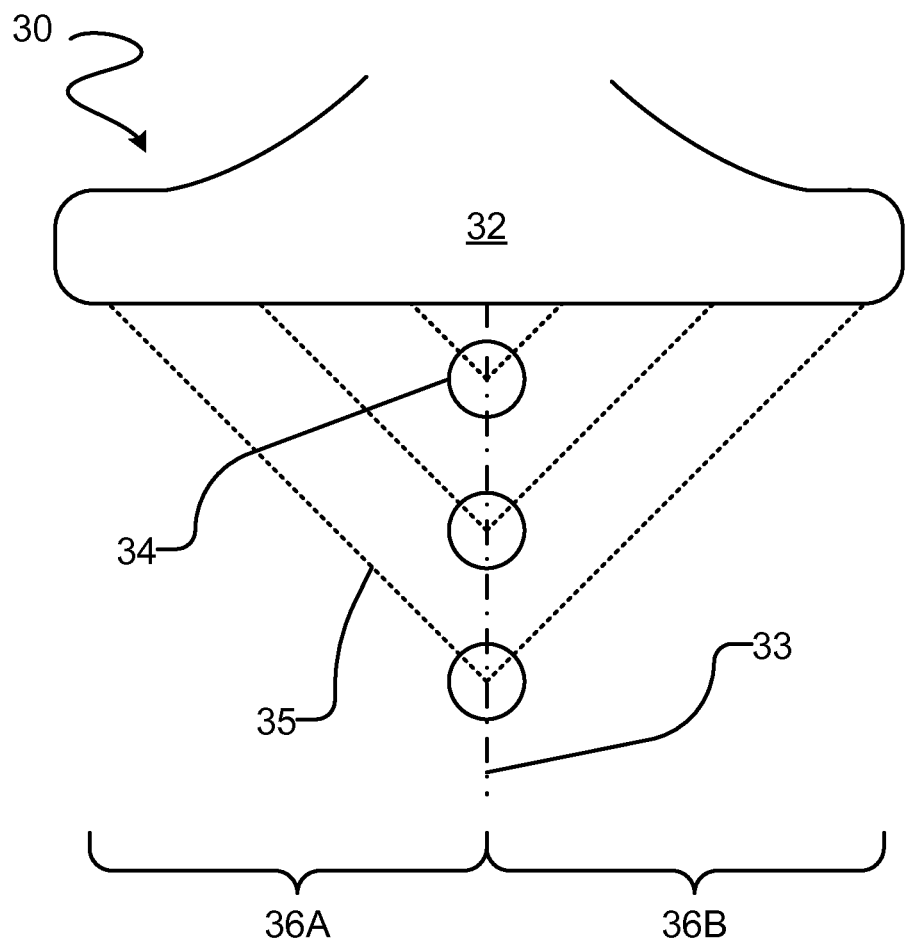
FIG. 3 is a schematic elevation view of a vector Doppler system.

FIG. 3 shows a vector Doppler ultrasound system 30 according to an example embodiment. Transducer 32 emits ultrasound pulses. In the illustrated embodiment, transducer 32 transmits ultrasound pulses along path 33. Sample volumes 34 lie along path 33. Sample volumes 34 are discrete from one another and spaced apart in some embodiments. In other embodiments some or all sample volumes 34 are abutting and/or overlapping with other sample volumes 34.

Some ultrasound echoes caused by reflections of transmitted pulses off of scattering centres in volumes 36 travel along return paths 35 to transducer 32. Transducer 32 receives such echoes in separate first 36A and second 36B channels. Each of channels 36A and 36B may comprise one or more transducer elements. In the illustrated embodiment, the angle of return paths is approximately 45 degrees. The angle of return paths may vary and in some embodiments is in the range of 20 to 90 degrees.

In embodiments, first and second channel data may be sampled simultaneously, alternately, or sampling of each channel may be interleaved with transmit pulses. Simultaneous sampling may provide the same pulse repetition frequency (PRF) as normal PW Doppler, thus preserving the range of Doppler shifts (and thus velocities) that may be detected. In addition, simultaneous sampling ensures that the velocities measured from the first and second channels are synchronized, which permits the principal velocity to be reconstructed by the two velocities measured at the same time. Where sampling of each channel is transmit-interleaved (e.g., transmit pulse, receive reflections on first channel, transmit pulse, receive reflections second channel), the PRF will be reduced by half and there will be a slight time offset between the left and right receiving. The offset can be compensated through interpolation in the processing stage.

There are alternative ways to process the collected channel data to obtain a measurement of the true blood flow velocity. According to one example method, the RF data corresponding to the sample volume that is received in the left and right channels is first down-mixed with sine and cosine waves at the transmit frequency to generate inphase (I) and quadrature (Q) components for each channel. A high pass filter, such as, for example, an infinite impulse response filter, may be used on the I and Q data to remove the influence from nearly stationary tissues on velocity estimation.

Multiple I and Q data generated from channel data corresponding to consecutive pulses are passed to autocorrelation velocity estimators. As new I and Q data enters a velocity estimator, the oldest data in the estimator is removed. In some embodiments I and Q data from 8 to 10 consecutive pulses is used in the autocorrelation velocity estimator. Where the intermittent transmit-and-receive method is used to obtain data for multiple channels in interleaved fashion, additional I and Q data sets may be used in one or more of the channels to facilitate time-synchronization of velocity estimates among the channels.

Figure 3A:
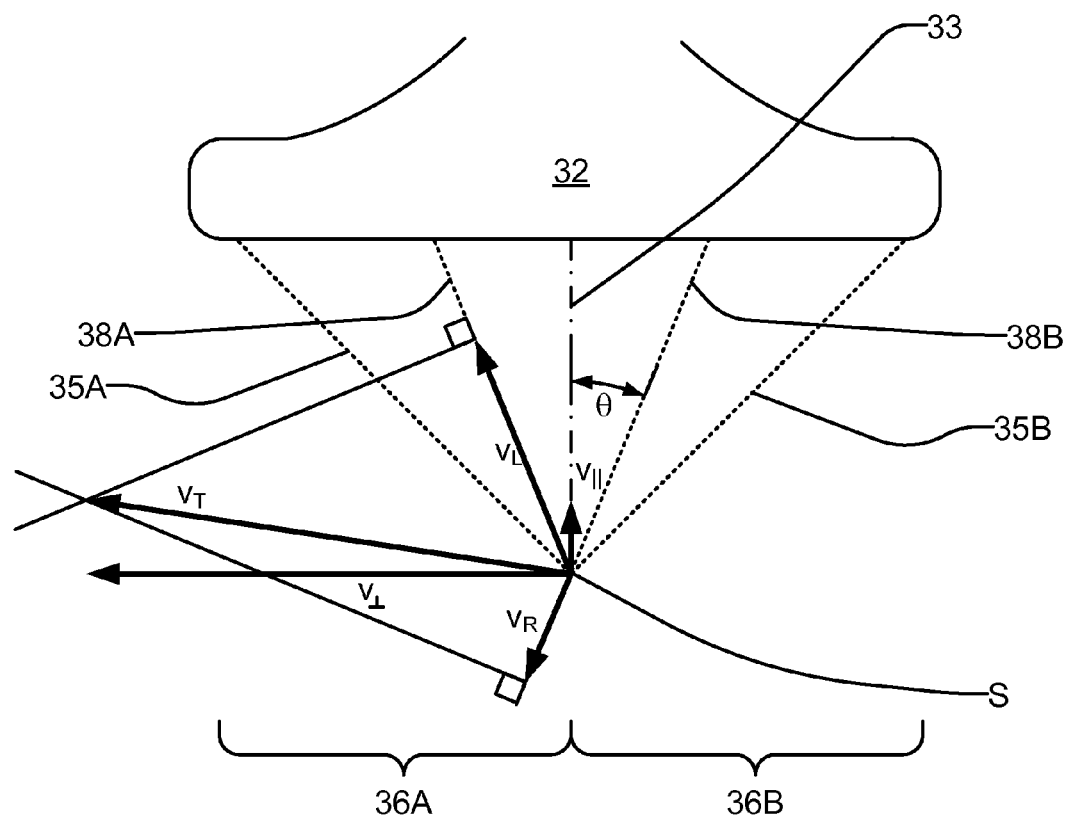

FIG. 3A illustrates the determination of a the velocity of blood flow from Doppler ultrasound velocity estimates. Since vector Doppler ultrasound uses a plurality of receiving and/or transmitting channels (e.g., left and right receive channels 36A and 36B), a plurality of frequency shifts are measured for each scattering location. Each frequency shift corresponds to the component of blood flow velocity at the particular scattering location that is parallel to the bisector of a transmit path to and a return path from the particular scattering location. In FIG. 3A, velocity components $V_L$ and $V_R$ lie along the bisectors 38A and 38B, respectively, of the angles between transmit path 33 and return paths 35A and 35B, respectively. Velocity components $V_L$ and $V_R$ are the projections of the true velocity vector $V_T$ onto bisectors 38A and 38B, respectively. True velocity vector $V_T$ may be constructed as the vector sum of its components perpendicular to the transmit axis ($V_\perp$) and parallel to the transmit axis ($V_\parallel$).

For receive channels that are symmetric about the transmit axis of the ultrasound probe, as in FIGS. 3 and 3A, the vector difference of the measured velocity components ($V_L - V_R$), multiplied by a scale factor ($1/\sin\theta$), yields the magnitude of the component of velocity perpendicular to the transmit axis ($|V_\perp|$), and the sum of the measured velocity components ($V_L + V_R$), multiplied by a scale factor ($1/(1+\cos\theta)$), yields the magnitude of the component of velocity parallel the transmit axis ($|V_\parallel|$). The true velocity vector of the blood flow in the sample volume (magnitude ($V_T$) and angle ($A_T$)) may then be reconstructed from the vector sum of the perpendicular velocity vector $V_\perp$ and axial velocity vector $V_\parallel$ by straightforward trigonometric operations. In embodiments where receive channels are not symmetric about the transmit axis, well known trigonometric relationships can be used to construct the true velocity vector from two or more measured velocity components.

In embodiments where only two velocity components are measured, the true velocity vector is the projection of the velocity of blood flow onto the plane defined by the paths from the sample volume to the receiving transducers. In embodiments where more than two different velocity components are measured, the true velocity vector may be representative of the actual velocity of the blood flow in the sample volume. A velocity estimate in three-dimensional space may be constructed from three or more different velocity components using known approaches, such as those disclosed in U.S. Pat. No. 6,589,179, Criton et al., and U.S. Pat. No. 5,701,898, Adam et al.

In embodiments, a controller may be configured to generate vector Doppler information according to any suitable method. Such a controller may be configured to store generated vector Doppler information in a memory. For example, a generated true velocity vector may be stored in a memory as true velocity magnitude and angle pair.

In some embodiments, a vector Doppler ultrasound unit, which may be of a type which is commercially available, produces a sequence of vector Doppler information for one or more sample volumes. The vector Doppler information may comprise, for example:
 true velocity magnitude and angle;
 true velocity components perpendicular to the transmit axis ($V_\perp$) and parallel to the transmit axis ($V_\parallel$);
 measured velocity components $V_L$ and $V_R$;
 the like.
In some embodiments, the vector Doppler unit generates such vector Doppler information at a rate of at least 5 kHz.

A controller may be configured to store generated vector Doppler information in data structures which associate the generated vector Doppler information with the sample volumes in the body of a patient to which the information pertains. For example, a controller may be configured to generate vector Doppler information for a location in the body of patient that is specified by a user-positionable cursor overlaid on a B-mode image. In some embodiments, the controller is configured to store the generated vector Doppler information in a data structure that associates the information with coordinates corresponding to the location of the user-positionable cursor on a B-mode image.

In embodiments, a controller may be configured to store generated vector Doppler information in data structures which associate the generated vector Doppler information with corresponding times to which the items of vector Doppler information pertain. For example, a controller may be configured to store generated vector Doppler information in a data structure that associates the information with a timestamp, counter or the like, corresponding to the time at which the data used to generate the information was acquired. In some embodiments, a controller may be configured to store sequentially acquired vector Doppler information as a sequence of data records, such as records stored sequentially in a continuous range of memory locations, a linked list, or the like.

Figure 4:
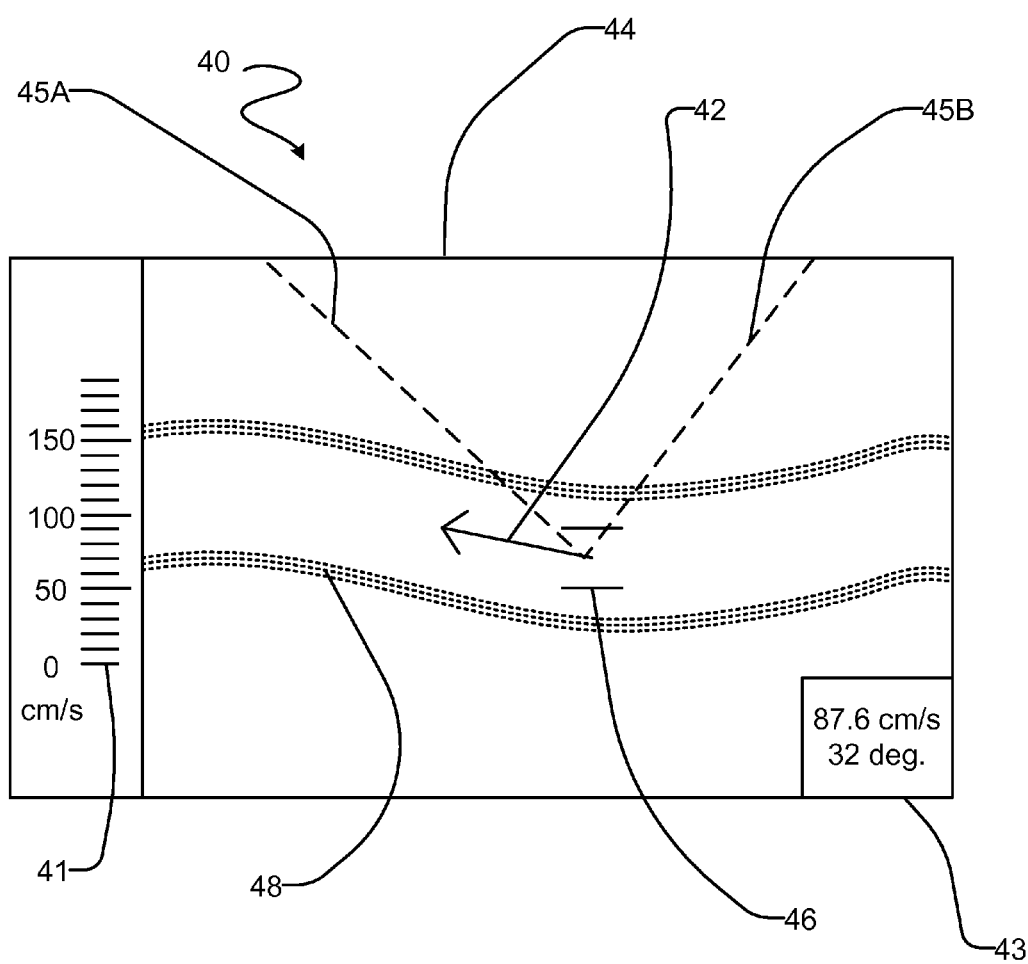
FIG. 4 is a schematic view of a display according to an example embodiment.

FIG. 4 shows a display 40 of a true velocity vector displayed as a vector-marker, namely arrow 42, overlaid on a B-mode image 44 of a region containing the sample volume for which the velocity vector was determined. In some embodiments the true velocity vector is generated continually and display 40 is updated in real-time to show the changing magnitude and orientation of the measured blood flow. Cursors 46 indicate the boundaries of the sample volume for which blood flow velocity is being determined. In display 40, cursors 46 are positioned on image 44 to lie within the outline of a blood vessel 48. In the illustrated embodiment, the length of arrow 42 corresponds to the magnitude of the true velocity vector and its orientation corresponds to the angle of the velocity vector.

In the illustrated embodiment, display 40 comprises a scale 41 that relates the length of arrow 42 to numeric velocity magnitude values. Display 40 also comprises a numeric representation 43 of scalar blood flow characteristics determined from the vector blood flow measurements, namely the magnitude and angle of the true velocity of the measured blood flow.

The orientation of arrow 42 indicates the direction of the flow of blood in the sample volume relative to the anatomical structures shown on B-mode image 44. Spatial correspondence between the displayed direction of the measured blood flow and the anatomical structures depicted in the B-mode image may be achieved by acquiring the data for the B-mode image and the blood flow velocity measurement at substantially the same time using the same transducer. Where this is done, an interleaving transmitting and receiving strategy for Doppler and B-mode pulses may be used. Interpolation between consecutive I and Q data sets may be used to estimate the I and Q data for time intervals during which B mode pulses are being transmitted and received. In some embodiments, the same pulses may be used for B-mode imaging and Doppler measurement. Alternatively, spatial correspondence between the displayed direction of the measured blood flow and anatomical structures depicted in the B-mode image may be achieved by aligning separately acquired B-mode image data and blood flow velocity data using position and orientation information from sensors located on the transducer(s) used to acquire the data, as described, for eg. in co-pending application No. 61/180,050, filed 20 May 2009 and entitled Ultrasound Systems Incorporating Spatial Position Sensors and Associated Methods, which is herein incorporated by reference.

Arrow 42 may indicate velocity magnitude by means other than length. For example, the color and/or brightness of arrow 42 may indicate the magnitude of the determined velocity. In some embodiments, both the color and/or brightness and the length of arrow 42 indicate the magnitude of the true velocity vector. In some embodiments, a display 40 includes a color-scale and/or brightness scale that associates the range of colors/brightenesses that arrow 42 may take-on with a numeric range of velocity magnitudes.

In embodiments, a controller may be configured to generate a display of a vector-marker using vector Doppler information, such as a true velocity angle and magnitude pair. For example, a controller may be configured to determine display characteristics of a vector-marker, such as orientation and length, by applying a true velocity angle and magnitude pair to a function, a look-up table, a logic circuit or the like.

Users may choose to measure blood flow velocity in different sample volumes by moving cursors 46 to various locations on B-mode image 44. In embodiments, users can move cursors 46 using user input devices, such as computer mice, trackballs, paired knobs, keypads, touchscreens, or the like. When cursors 46 are moved, the gating of the received pulses may be adjusted to sample pulses corresponding to reflections originating in the location of the sample volume.

Because blood flow velocity may be determined more accurately when pulses are received from the sample volume along paths that have components parallel to the direction of the flow of blood in the sample volume, display 40 may provide information to guide the positioning of cursors 46 on image 44 and/or positioning of the ultrasound probe used to acquire image 44. For example, display 40 comprises graphical indications 45A and 45B of the bisectors of the angles between the path from the transmitting transducer element to the sample volume indicated by cursors 46 and the paths from the sample volume to the receive transducers. A controller may generate graphical indications 45A and 45B for example by determining a location of the sample volume in a suitable coordinate system and providing the location as input to a function based on the geometry of probe transducer elements.

In some embodiments, graphical indications 45A and 45B indicate the return paths from the sample volume to the receive transducers. Graphical indications 45A and 45B are not necessarily symmetric with respect to cursors 46. For example, in some embodiments, ultrasound pulses are transmitted at different angles. In some embodiments, display 40 comprises a line segment or other graphical indication indicative of the direction normal to the surface of the ultrasound transducer.

In some embodiments, a plurality of cursors is provided, enabling a user to specify several separate locations for which blood velocity measurements will be acquired. Multiple vector-markers indicative of instantaneous blood-flow velocity measurements at the locations specified by the cursors may be provided. Doppler frequency shifts may be estimated at multiple locations by steering transmitting ultrasound pulses to pass through the locations specified by the cursors and then receiving signals from each of the locations.

In some embodiments, one or more cursors in the form of a line segment (or end-points of a line segment) are provided, and multiple vector-markers are provided at spaced apart locations along each line segment cursor. In some such embodiments, the line segment cursor(s) may be rotated and/or positioned by a user to lie along or across a B-mode image of a blood vessel to obtain true velocity vectors for different sample volumes in, along and/or across the vessel. In some embodiments, a user control is provided for determining the length(s) of line segment cursor(s).

Figure 5:
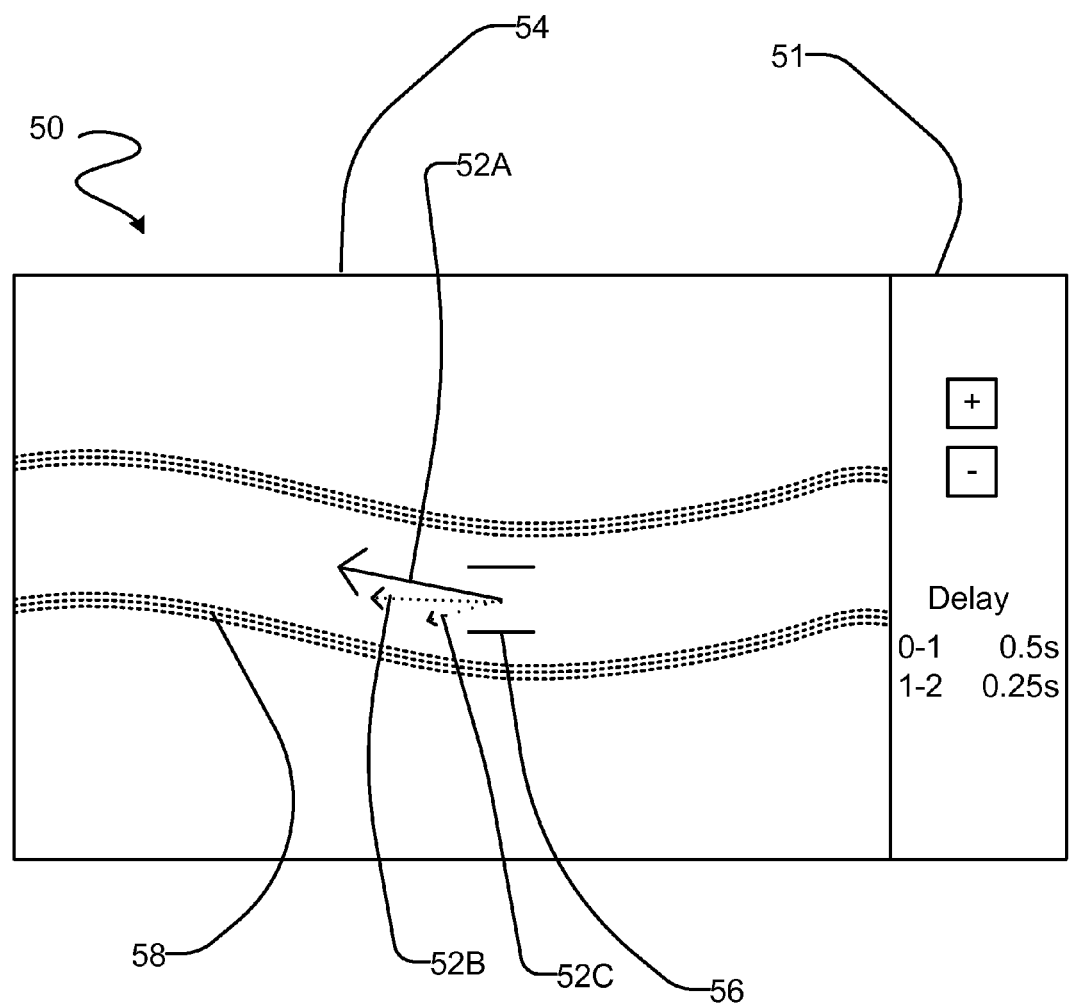
FIG. 5 is a schematic view of a display according to an example embodiment.

In some embodiments, time-persistence is applied to displayed vector-markers so that time-varying characteristics of the blood flow may be perceived. FIG. 5 shows a display 50 in which arrows 52A, 52B and 52C overlaid on B-mode image 54 correspond to true velocity vectors acquired at different times. Arrows 52A, 52B and 52C appear differently so the time relations between them may be perceived. Specifically, arrows 52B and 52C have smaller end points and are displayed more faintly than arrow 52A. Other means, or combinations of means, for distinguishing arrows representing flow velocities measured at different times may be used, such as, for example, color, line-style or the like. In some embodiments, a controller determines an arrow 52 then displays it for some pre-determined number of time periods, changing its appearance in each time period. A new arrow may be added every time period or every so many time periods.

Arrow 52A corresponds to the most recently determined true velocity vector. Arrows 52B and 52C correspond to earlier determined true velocity vectors. The time between the acquisition of the data used to construct the true velocity vectors corresponding to arrows 52A, 52B and 52C may be greater than the time between consecutively determined true velocity vectors. In some embodiments, the time separating arrows 52A, 52B and 52C is in the range of 0.05 to 1 seconds. In some embodiments, the number of arrows displayed and the time intervals between each of them is user-selectable. For example, a user may specify the number of arrows to be displayed and/or the time intervals between each of them by manipulating a control provided on display 50, such as control 51, by means of a keyboard, mouse or other input device.

In embodiments, a controller may be configured to generate a display of time-persisted vector-markers using vector Doppler information, such as a true velocity angle and magnitude pairs, associated with different times. A controller may be configured to determine a display attribute for a vector-marker based on an difference between the time associated with the vector Doppler information corresponding to the vector marker and another time. For example, a controller may be configured to determine a difference between a timestamp, counter value, memory location or the like associated with a true velocity angle and magnitude pair, and a current like indicia (e.g., the current time), and to determine a display attribute for a vector-marker corresponding to the pair based on the difference. In another example, a controller may be configured to determine a difference between the timestamps, counter values, memory locations or the like associated with different true velocity angle and magnitude pairs, and to determine a display attribute for one or both of the vector-markers corresponding to the pairs based on the difference.

A B-mode image over which graphical velocity information is overlaid may be updated continually. In some embodiments, the B-mode image is updated at the same rate as the graphical velocity information. In other embodiments, the B-mode image is updated less frequently than the graphical velocity information. The B-mode image may be updated infrequently or not at all (e.g., the B-mode image may be a still image).

Figure 6A:
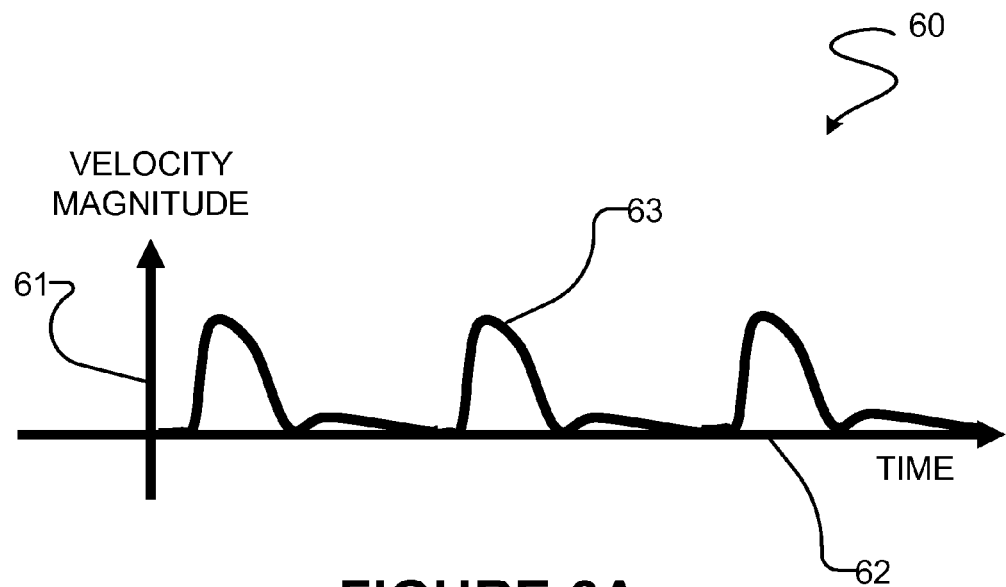
FIG. 6A is a graph of velocity magnitude versus time according to an example embodiment.
Figure 6B:
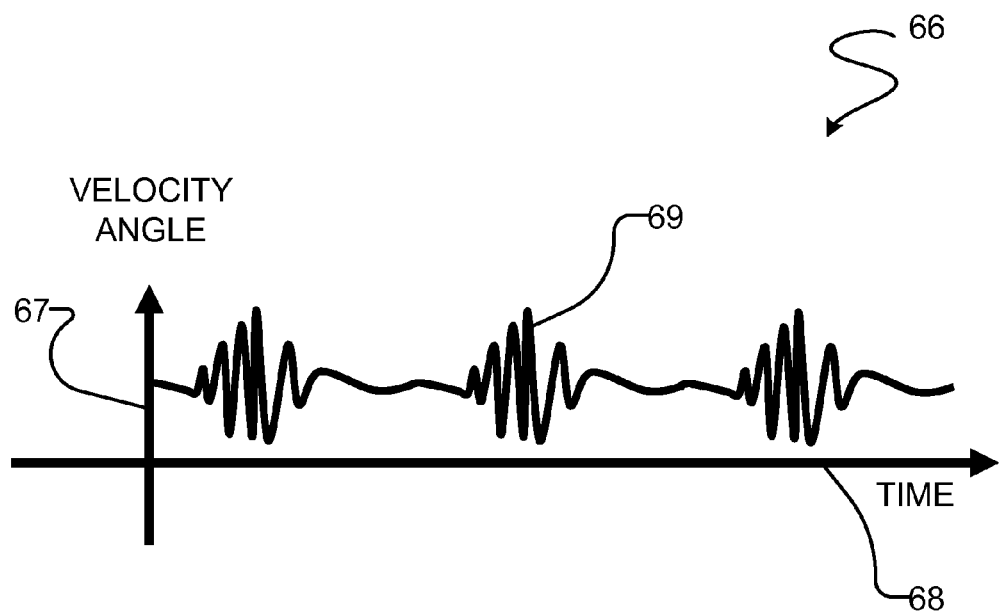
FIG. 6B is a graph of velocity angle versus time according to an example embodiment.

Some embodiments provide a display comprising one or more plots of scalar blood flow characteristics (e.g., velocity magnitude, velocity angle, etc.) derived from vector blood flow measurements (e.g., true velocity) over time. FIGS. 6A and 6B show, respectively, example graphs 60 and 66, either or both of which may be included in displays according to some embodiments. In graph 60, vertical axis 61 represents the magnitude of the true velocity vector, horizontal axis 62 represents time and curve 63 indicates the magnitude of the true velocity vector at different points in time. In graph 66, vertical axis 67 represents the angle of the true velocity, horizontal axis 68 represents time and curve 69 indicates the angle of the true velocity vector at different points in time.

The angle of the true velocity vector may be determined with respect to a fixed reference (e.g., the ultrasound transmit axis) or a user configured reference (e.g., a line cursor positioned on a B-mode image). Axes 62 and 68 share the same timescale and may be near one another and aligned such that there is time correspondence between vertically aligned points on curves 63 and 69. Graphs 60 and 66 may be continually updated with current velocity information. In some embodiments, curves 63 and 69 scroll across their respective plots.

In some embodiments, a user controlled cursor for specifying a particular velocity direction is provided, and the magnitude of the component of the true velocity vector along the direction specified by the cursor is plotted over time on a display. For instance, a user may use a cursor to indicate a direction parallel to the axis of a vessel that contains the sample volume to obtain a plot of the magnitude of the component of the true velocity vector parallel to the vessel axis over time.

In some embodiments, a cursor specifying perpendicular directions (e.g., a cross, L-shape, or the like) is provided, and corresponding perpendicular velocity components are plotted over time on a graph. Some embodiments provide a directional cursor that is positionable to indicate the location of the sample volume and rotatable to indicate the component(s) of velocity to be plotted.

In some embodiments, a controller is configured to determine the magnitude of the component of the true velocity vector along one or more user-specified directions. A controller may be configured to determine the magnitude of the component of the true velocity vector along a user-specified direction by, for example, computing the projection of the true velocity vector onto a line parallel to the user specified direction.

True velocity vectors may be generated at high rates. For example, if the PRF is 8 KHz a new true velocity vector may be determined 8000 times per second. In some embodiments, values of a scalar blood flow characteristic determined over a time interval may be plotted together. Taking the example just given, rather than plotting 8000 velocity magnitude values at separate points along a timescale every second, batches of two or more values may be plotted together at single locations along the timescale that correspond to the time intervals over which the corresponding values were collected. In some embodiments, the number of values that are plotted together is user configurable. In some embodiments, in the range of 1 to 1000 values are plotted together. In some embodiments, values are assigned to time-slots and all values corresponding to a same time slot are plotted together. In some embodiments, each time slot corresponds to an interval in the range of 0.1 ms to 100 ms.

In some embodiments, a plurality of values of a scalar blood flow characteristic determined in a time interval are plotted together as a fewer number of values (e.g., one value) determined by a mathematical function, such as, for example, a mean, median, sum or the like. For example, each point plotted in graphs 60 and 66 may correspond to plots of the output of a mathematical function that takes as input the values of velocity magnitude and angle, respectively, determined in a time interval corresponding to each plotted point. By controlling the number of values that are combined together (i.e., the length of the time interval corresponding to points on the plotted curve), a user may "zoom" in and out on the plotted curve.

In embodiments, a controller may be configured to generate plots of scalar blood flow characteristic values over time using vector Doppler information, such as a true velocity angle and magnitude pairs, associated with different times. For example a controller may be configured to plot a velocity magnitude and/or angle value at a point identified by the output of a the application of a timestamp, counter value, memory location or the like to a function, lookup table, logic circuit or the like. A controller may be configured to combine a plurality of values of a scalar blood flow characteristic determined in a time interval using a mathematical function, and to plot the output of the function as a single point. In some embodiments, a controller is configured to ascertain a set of values of a scalar blood flow characteristic corresponding to a time interval by comparing timestamps, counter values, memory locations, or the like, associated with the values to timestamps, counter values, memory locations, or the like that define a range corresponding to the time interval.

Figure 7A:
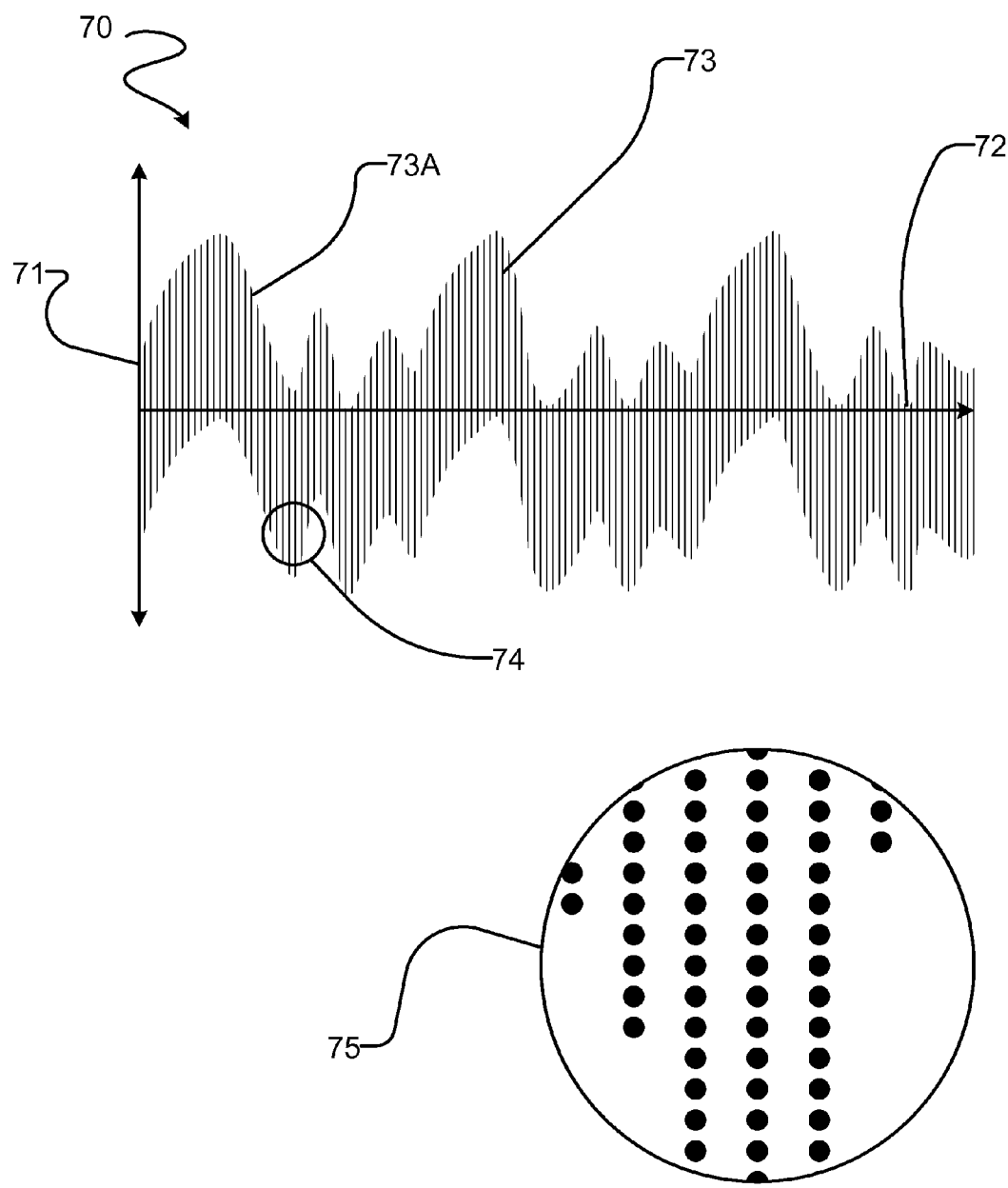
FIG. 7A is a graph of velocity magnitude versus time according to an example embodiment.

In some embodiments, several values of a scalar blood flow characteristic determined in a time interval are plotted individually at a single location along a timescale that corresponds to the time interval in which the several values were determined. FIG. 7A shows a graph 70 of velocity measurements over time. In graph 70, vertical axis 71 represents the magnitude of the true velocity vector and horizontal axis 72 represents time. Curve 73 comprises values plotted so that values obtained within a time interval are plotted together in vertical alignment at a location along horizontal axis 72 that corresponds to the time interval.

Curve 73 has the appearance of a series of vertical lines 73A because two or more different values are plotted for each time interval. Magnified view 75 shows detail of values plotted in region 74 of curve 73. The length of each vertical line 73A may be an indication of the variability of the velocity measurements within the corresponding time interval. Large variability in velocity magnitude and/or angle within a short time interval may indicate blood flow turbulence.

Figure 7B:
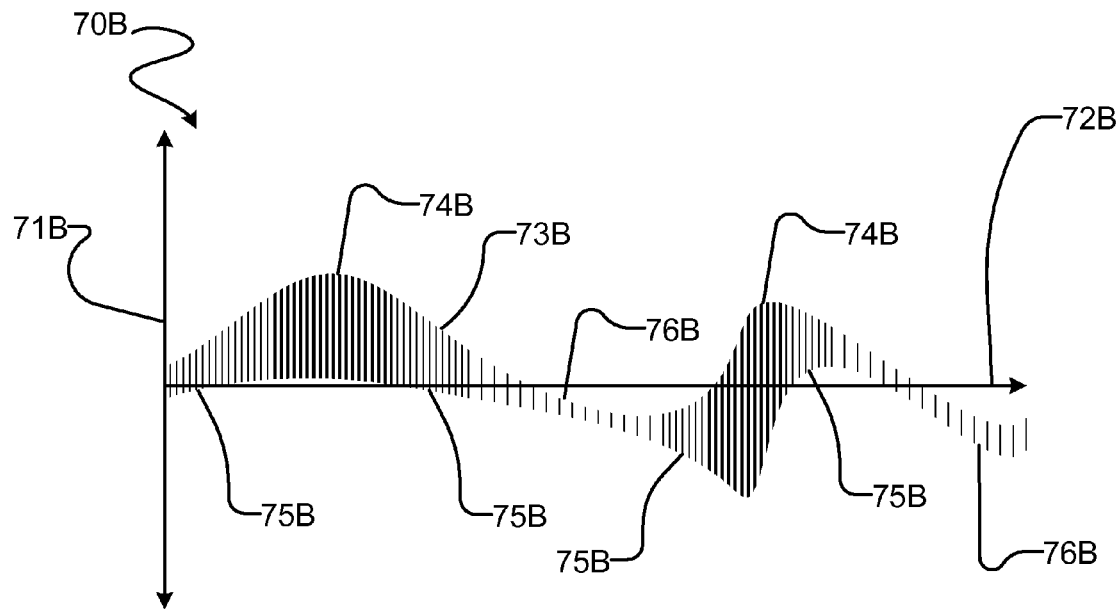
FIG. 7B is a graph of velocity magnitude versus time according to an example embodiment.

FIG. 7B shows a graph 70B of velocity measurements over time. In graph 70B, vertical axis 71B represents the angle of a true velocity vector and horizontal axis 72B represents time. Curve 73B comprises values plotted so that values obtained within a time interval are plotted together in vertical alignment at a location along horizontal axis 72B that corresponds to the time interval. Curve 73B is plotted with different display attributes (intensity, shown as darkness in FIG. 7B) to mark differences in the degrees of variability among velocity measurements.

Regions 74B comprise velocity measurements with relative large variability. Measurements in regions 74B are plotted with greater intensity. Regions 76B comprise velocity measurements with relative small variability. Measurements in regions 76B are plotted with less intensity. Regions 75B comprise velocity measurements with variability in between the variability of velocity measurements in regions 74B and 76B. Measurements in regions 75B are plotted with intermediate intensity. Other display attributes may be used to indicate the variability of velocity measurements, for example, color, brightness, or the like. Some embodiments comprise a display attribute scale that associates particular display attributes in a range of a display attributes with numeric values (e.g., percentages) or ranges of numeric values, indicative of the variability among of velocity measurements represented by the particular display attributes. Displays comprising graphs like graph 70B may enable users to assess at a glance the degree of variability of velocity magnitude and/or angle measurements, and/or the times at which variability of such measurements is large and/or small.

In embodiments, a controller may be configured to generate a plot comprising several scalar blood flow characteristic values plotted at a single location along a timescale. Given a time range and plot size specified by user input and/or characteristics of a display on which the plot is to be displayed (e.g., resolution), the controller may divide the time range into an number of time intervals that fits the time axis of the plot. For example, a controller may be configured divide a time range of m units (e.g., time, samples, etc.) that is to be displayed across n locations (e.g., pixels of horizontal resolution) into equal intervals of m/n units each, with each interval corresponding to one of the n locations along the timescale.

For a given location along the timescale, the controller may be configured to ascertain a set of corresponding scalar blood flow characteristic values to be plotted at the location. For example, given a set of records comprising velocity magnitude and/or angle values and associated index time values (e.g., timestamps, counter values, memory locations or the like) a controller may be configured to:
  determine a reference time index value (e.g., a timestamp, counter value, memory location or the like) corresponding to the start of the time range and timescale;
  determine a number of velocity magnitude and/or angle values to be plotted at each location along the timescale;
  determine an interval index offset corresponding to the number of velocity magnitude and/or angle values to be plotted at each location along the timescale;
  for each location along the timescale, compute a location index offset equal to the product of the interval index offset and an index value of the location along the timescale (e.g., horizontal axis coordinate);
  for each location along the timescale, compute a location start index equal to the sum of the location index offset and the reference time index value;
  for each location along the timescale, compute a location end index equal to the sum of the location start index and the interval index offset; and
  for each location along the timescale, ascertain the set of velocity magnitude and/or angle values to be plotted at the location as the set of velocity magnitude and/or angle values contained in the records having indexes running from the location start index offset to the location end index.

In some embodiments, the controller may be configured to use a particular interval index offset (e.g., plot size and/or time range) indicated by user input. Such embodiments may provide "zoom" functionality with respect to the timescale.

In some embodiments, a controller is configured to control the number of scalar blood flow characteristic values that are displayed on a timescale and/or the time spanned by scalar blood flow characteristic values displayed on a timescale by controlling the rate at which scalar blood flow characteristic values are generated, selecting subsets of scalar blood flow characteristic values for display, controlling the number of scalar blood flow characteristic values that are displayed together at a single location along the timescale, and/or combining scalar blood flow characteristic values for display. For example, in some embodiments:
  a controller obtains a stream of scalar blood flow characteristic values and is configured to select every $n^{th}$ scalar blood flow characteristic values for display;
  a controller is configured to group consecutively generated (or selected) scalar blood flow characteristic values into groups of m measurements and plot measurements assigned to the same group together at a single location along a timescale;
  a controller is configured to group scalar blood flow characteristic values generated (or selected) in time periods of duration T into groups and plot values assigned to the same period-group together at a single location along a timescale;
  a controller is configured to combine groups of m consecutively generated (or selected) scalar blood flow characteristic values into a single value and plot the value; and/or
  a controller is configured to combine groups scalar blood flow characteristic values generated (or selected) in time periods of duration T into a single value and plot the value.

In some embodiments, a controller is configured to determine an indication of variability of a scalar blood flow characteristic. For example, a controller may be configured to compute a statistic, such as range, standard deviation, variance or the like, of a set of values of a scalar blood flow characteristic that are plotted together. In some embodiments, a controller is configured to determine a display attribute for displayed scalar blood flow characteristic values corresponding to an indication of variability of the values. A controller may be configured to determine a display attribute corresponding to an indication of variability of scalar blood flow characteristic values using a function, lookup table, logic circuit, or the like. In some embodiments, the controller is configured to display scalar blood flow characteristic values using a display attribute corresponding to an indication of variability of the blood velocity measurements. A controller may be configured to display a numerical value corresponding to an indication of variability of the scalar blood flow characteristic values. A controller may be configured to determine a numerical value corresponding to an indication of variability of scalar blood flow characteristic values using a function, lookup table, logic circuit, or the like.

In some embodiments, the appearance of sudden changes in plotted scalar blood flow characteristic values is avoided by plotting values near the boundaries between time intervals in the time intervals on both sides of the boundaries. This and/or other techniques for smoothing the appearance of data one or more time interval boundaries may be implemented in embodiments.

The number of discrete values in the range of a scalar blood flow characteristic may exceed the resolution of typical displays. Where a display does not have sufficient resolution to display discretely all of the values in a range of values, values in sub-ranges of values may be binned together such that all measurements within a sub-range are plotted at a single location along a value axis. Sub-ranges may be sized equally, such that all of the sub-ranges are substantially the same size, or may be sized unequally. The relationship between the sizes of unequally sized sub-ranges may logarithmic, for example, so as to highlight particular ranges of values. Any suitable number of sub-ranges may be provided, and in some embodiments is user configurable.

In embodiments, a controller may be configured to plot values in sub-ranges of values together at a single location along a value axis. For example, a controller may be configured to apply values to be plotted to a function, lookup table, logic circuit or the like and to plot a point at a value axis location corresponding to the output of the function, lookup table, logic circuit of the like. In some embodiments, a controller may be configured to use a particular function, lookup table, logic circuit or the like indicated by user input. Such embodiments may provide "zoom" functionality with respect to the value axis.

Figure 7C:
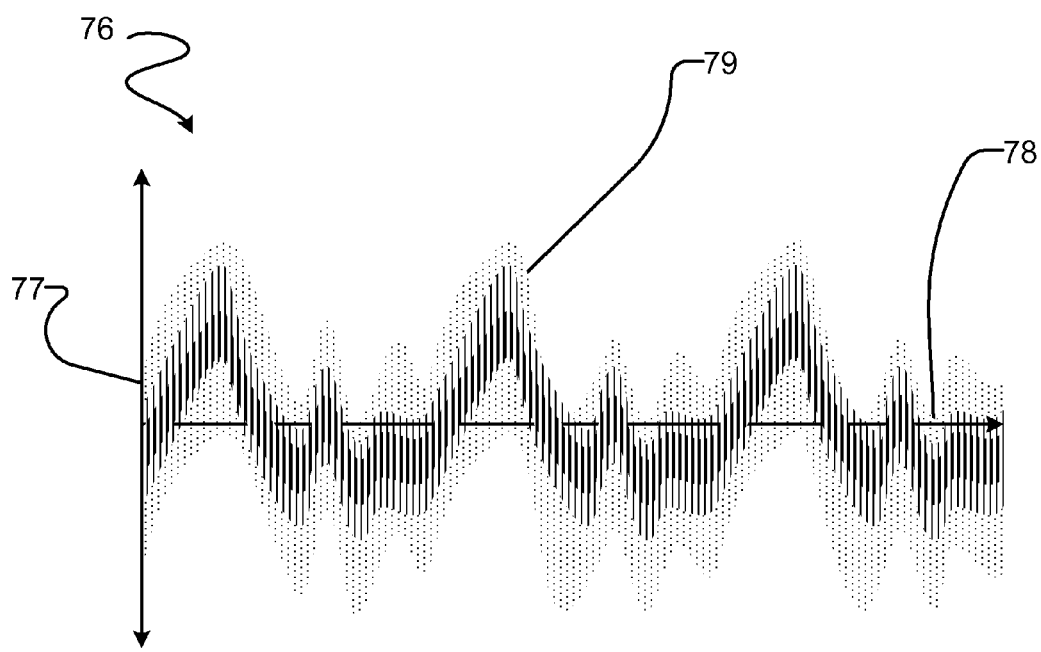
FIG. 7C is a graph of velocity magnitude versus time according to an example embodiment.

In some embodiments, the relative prevalence of similar values within a time interval may be indicated by assigning plotted points display attributes, such as color, brightness or the like, corresponding to the number of values that each point represents. FIG. 7C shows a graph 76 of velocity values over time. In graph 76, vertical axis 77 represents the magnitude of the true velocity vector and horizontal axis 78 represents time. Curve 79 comprises points corresponding to time-intervals and value sub-ranges. Some points of curve 79 correspond to several different values corresponding to the same time-interval and value sub-range. The number of values represented by points on curve in 79 is indicated by the intensity (darkness in FIG. 7C) of the point. Other display attributes may be used to indicate the number of values represented by a point, for example, color, brightness, or the like. Some embodiments comprise a display attribute scale that associates particular display attributes in a range of a display attributes with numeric values (e.g., percentages) or ranges of numeric values, indicative of the number of values represented by the particular display attributes. Displays comprising graphs like graph 76 may enable users to assess at a glance the degree of variability of velocity magnitude and/or angle measurements.

In some embodiments, a controller may be configured to track the number of values plotted together at a single location along a value axis, and to use this tracking information to determine a display attribute of a plotted point. For example, given a set of values to be plotted at a single location along a timescale, a controller may be configured to apply the values in the set to a first function, lookup table, logic circuit or the like, and for each output yielded by the application of the values, increment a counter corresponding the value of the output. The controller may be configured to determine a display attribute for a plot point corresponding to each counter by applying the value of the counter to a second function, lookup table, logic circuit or the like. The controller may be configured to plot a point corresponding to each counter at a location corresponding to the output value of the function that corresponds to the counter.

Figure 8:
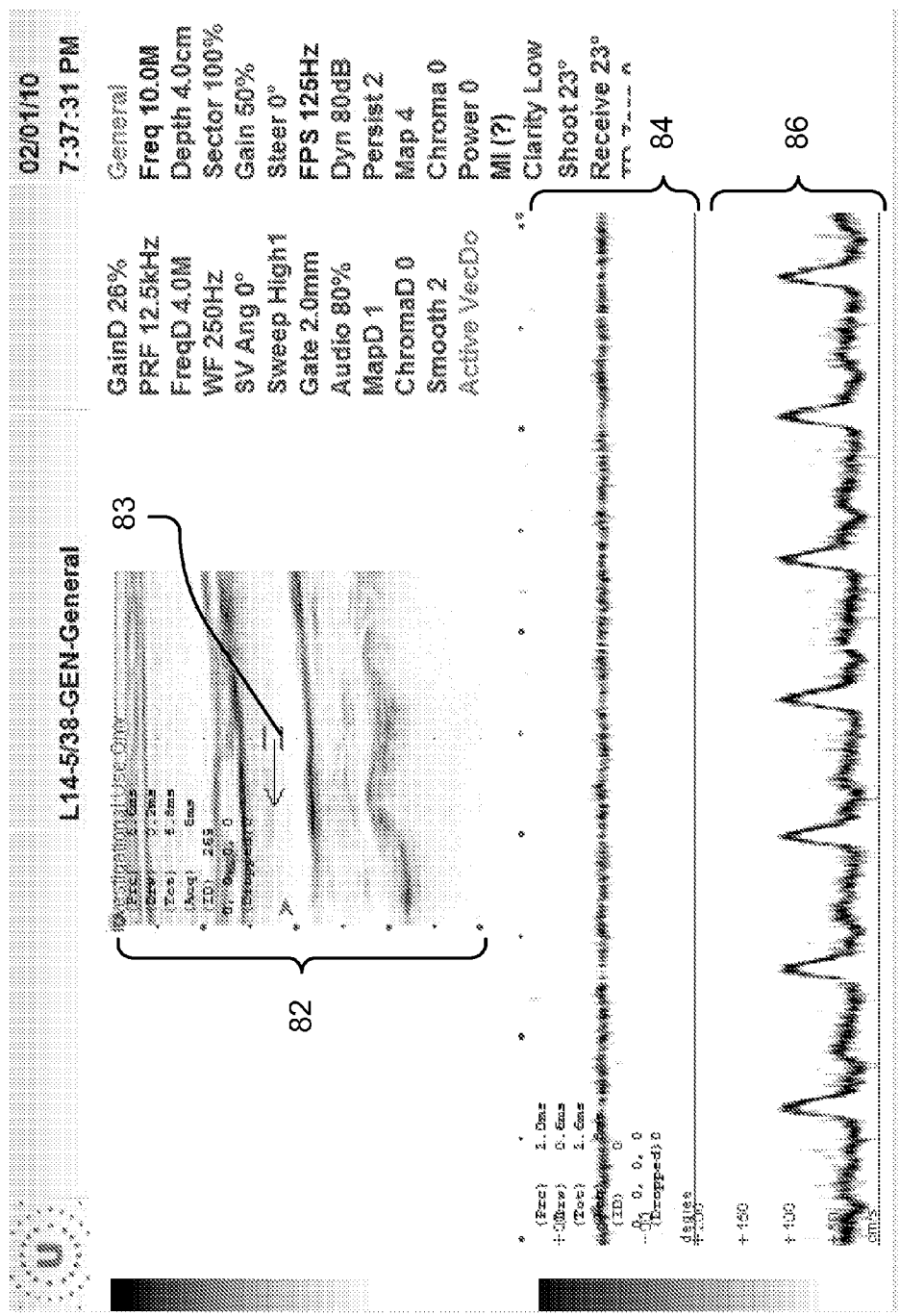
FIG. 8 is a display according to an example embodiment.

FIG. 8 shows a display 80 according to an example embodiment. The top portion of display 80 includes a graphical marker 83 indicating instantaneous blood flow velocity magnitude and angle overlaid on a B-mode image 82. The bottom portion of display 80 includes a graph 84 of velocity angle (ordinate) over time (abscissa) and a graph 86 of velocity magnitude (ordinate) over time (abscissa). In some embodiments, marker 83 represents the real-time current true velocity vector and plots 84 and 86 are scrolling graphs. Plots 84 and 86 comprise curves 85 and 87, respectively. Curves 85 and 87 are discrete; they comprise points whose locations correspond to particular ranges of value and time. The variance in brightness among the points of curves 85 and 87 corresponds to the prevalence of values in the ranges corresponding to the points.

In some embodiments, a cursor is provided for selecting a point in time along one or both of graphs 84 and 86, and marker 83 represents the instantaneous true velocity vector at the time indicated by the cursor. In some embodiments, the cursor is positionable along the timescale of graph 84 and/or 86 and marker 83 is continually updated to reflect the instantaneous true velocity vector at the time corresponding to the position of the cursor. In some such embodiments, graphs 84 and 86 may comprise snapshots of historical blood velocity information (i.e., graphs 84 and 86 may be static). Some embodiments provide a numerical display of velocity magnitude and/or angle values at the point in time indicated by the cursor.

In some embodiments, display 80 further comprises one or more plots of cardiac and/or respiratory activity, for example, an ECG trace and/or a respiration graph. In some such embodiments, the graph(s) of cardiac and/or respiratory activity have the same timescale as and are aligned with graph(s) of velocity magnitude and/or angle. In some embodiments, user controllable cursors are provided to identify scalar blood flow characteristic values corresponding to particular moments in the cardiac and/or respiratory cycle. For example, user controllable cursors may be used to indicate the points on graph 86 that typically correspond to peak systolic velocity, minimum forward diastolic velocity in unidirectional flow, maximum negative velocity in diastolic flow reversal or the like. Scalar blood flow characteristic values at the times corresponding to the positions of the user-controllable cursors may be displayed numerically on display 80. A control for capturing and storing in memory the scalar blood flow characteristic values corresponding to points on graphs 84 and/or 86 may be provided.

Some embodiments provide a controller configured to apply a signal analysis function to signals indicative of blood flow velocity, cardiac activity and/or respiratory activity to determine the timing of particular cyclical blood flow characteristics, such as peak systolic velocity, minimum forward diastolic velocity in unidirectional flow, maximum negative velocity in diastolic flow reversal or the like. A signal analysis function may identify patterns in signals indicative of blood flow velocity, cardiac activity and/or respiratory activity. The patterns identified may be characteristic of moments in the cardiac or respiratory cycles corresponding to particular cyclical blood flow characteristics. The timing of the occurrences of such characteristic patterns may be output by the signal analysis function. The occurrences may be identified, for example, by locating maxima or minima in the signals, identifying points at which the signals cross thresholds, identifying patterns in the signals, or the like.

A controller may be configured to use the timing of the occurrences to select blood flow velocity information corresponding in time to the particular cyclical blood flow characteristics. For example, an ECG provides a signal according to the voltage difference(s) between two or more electrodes, which signal indicates the electrical activity of one or more parts of the heart. A signal analysis function may provide a list of times at which the ECG signal exhibited a pattern characteristic of the moment in the cardiac cycle corresponding to peak systolic velocity. A controller may be configured to select blood flow velocity information contained in records associated with times corresponding to the list of times output by the signal analysis function.

In some embodiments, a controller is configured to apply a signal analysis function to historical signals indicative of blood flow velocity, cardiac activity and/or respiratory activity. In some embodiments, a controller is configured to apply a signal analysis function in real-time to signals indicative of blood flow velocity, cardiac activity and/or respiratory activity. A controller may be configured to use the timing of characteristic patterns to locate markers on a display to indicate the timing of the patterns. A controller may be configured to use the timing of characteristic patterns to automatically extract blood flow velocity information. In some embodiments, a controller may be configured to extract blood flow velocity information from a time-associated list of blood velocity information using timing information generated by the application of a signal analysis. In some embodiments, a controller may sample blood flow velocity information in real-time, for example, close in time to when the corresponding characteristic pattern occurs, according to timing information generated by the application of a signal analysis function to signals indicative of blood flow velocity, cardiac activity and/or respiratory activity.

User controllable cursors may be used to indicate the beginning and end of time intervals on graphs 84 and/or 86. Blood velocity characteristics in time intervals identified in this manner may be determined automatically. For example, a controller may be configured to determine peak blood velocity magnitude in a time interval by identifying the largest blood velocity magnitude measurement in the time interval. Blood velocity information in time intervals indicated by positions of cursors may be used to determine derivative blood flow information. For example, a controller may be configured to apply blood velocity information in a time interval to formulas or functions, such as for mean blood velocity magnitude, pulsatility index or the like. In some embodiments, derivative blood flow information may comprise time-derivatives of time-varying blood flow information. Derivative blood flow information, such as the results of such formulas or functions, may be displayed by a controller on a display.

Figure 9:
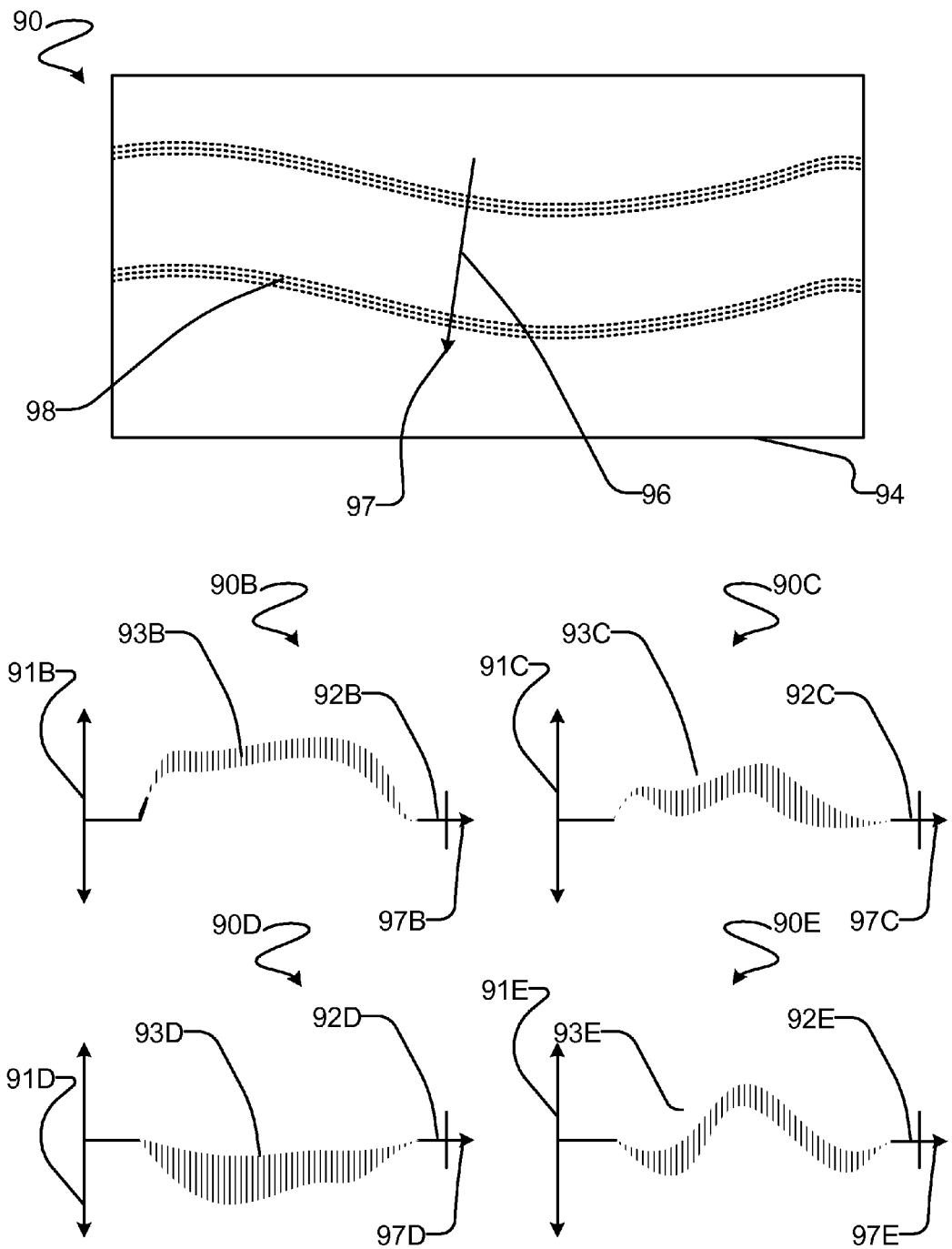
FIG. 9 is a display according to an example embodiment.

Some embodiments provide a display showing ranges of scalar blood flow characteristic values obtained over a time interval for a plurality of adjacent sample volumes. FIG. 9 shows a display 90 comprising a B-mode image 94 with a line segment cursor 96 on an image of a blood vessel 98 and blood velocity magnitude versus position graphs 90B, 90C, 90D and 90E. Cursor 96 extends across the outline 98 of a blood vessel. Cursor 96 is generally perpendicular to what outline 98 suggests are the walls of the blood vessel. The orientation and position of cursor 96 may be user adjustable. In some embodiments, one or more vector-markers indicating instantaneous blood flow velocity are displayed along cursor 96.

Graphs 90B, 90C, 90D and 90E show blood velocity magnitude information for sample volumes located in the plane of image 94 and along cursor 96. In graphs 90B, 90C, 90D and 90E, the vertical axes 91B, 91C, 91D and 91E represent the magnitude of the component of blood flow in the plane of image 94 and perpendicular to cursor 96. The horizontal axes 92B, 92C, 92D and 92E represent position along cursor 96. The arrow 97 at the end of cursor 96 corresponds to the ends of horizontal axes 92B, 92C, 92D and 92E that are capped by arrows 97B, 97C, 97D and 97E. Velocity measurements corresponding to locations along cursor 96 are plotted at corresponding locations along horizontal axes 92B, 92C, 92D and 92E. Curves 93B, 93C, 93D and 93E comprise points representing velocity measurements obtained in a time interval. Each of curves 93B, 93C, 93D and 93E corresponds to a different time interval. Where different measured velocity values are obtained for a given location in the blood vessel in a time interval, these measurements appear on curves 93B, 93C, 93D and 93E as vertically aligned points.

The time intervals of graphs 90B, 90C, 90D and 90E may be shorter than the duration of a cardiac or respiratory cycle. Graphs 90B, 90C, 90D and 90E may be useful for studying changes in blood flow velocity across the blood vessel outlined by outline 98 over time. For example, the vertical range of curves 93B, 93C, 93D and 93E may be indicative of the rate of change of blood flow velocity during the corresponding time intervals. In some embodiments, the time intervals corresponding to plots 90B, 90C, 90D and 90E are continuous, so that curves 93B, 93C, 93D and 93E appear to "flow" into one another (i.e., the lower envelope of curve 93B will approximate the upper envelope of curve 93C). In other embodiments, the time intervals corresponding to plots 90B, 90C, 90D and 90E are not continuous.

In some embodiments, display attributes are applied to curves 93B, 93C, 93D and 93E to indicate time-varying and/or spatially-varying characteristics of measured blood flow velocity. For example, measurements plotted on graphs 90B, 90C, 90D and 90E may be plotted with different display attributes to mark differences in the degrees of variability among velocity measurements, such as in the manner shown in graph 70B. The application of display attributes in this manner may serve to mark spatial regions (e.g., sample volumes corresponding to locations along horizontal axes 92B, 92C, 92D and 92E and along cursor 96) that exhibit levels of velocity measurement variability indicative of blood flow turbulence. Displays that mark spatial regions this way may enable users to more easily identify blood flow turbulence.

In some embodiments, display attributes are applied to cursor 96 to indicate time-varying and/or spatially-varying characteristics of velocity measurements obtained for sample volumes corresponding to cursor 96. For example, different parts of cursor 96 may be shown in different colors to indicate of the variability of velocity measurements obtained for sample volumes along cursor 96. Where this is done, users may be able to determine the existence and/or characteristics of blood flow turbulence conditions at locations depicted in B-mode image 94.

For instance, where cursor 96 corresponds to sample volumes in the vicinity of an arterial stenosis, the stenosis may cause local blood flow turbulence during the systolic phase. The periodic local blood flow turbulence may be reflected in increased variability of blood velocity measurements for the sample volumes in the vicinity of the stenosis. As a result, the portion of cursor 96 that corresponds to the region of local blood flow turbulence may have a pulsating appearance corresponding to the periodic changes in blood velocity measurement variability. Displays that indicate blood velocity measurement variability this way may enable users to identify locations of stenoses or other turbulence causing features, which may not be easily seen on B-mode images, and to estimate risk of blood vessel pathologies correlated with blood flow turbulence (e.g., plaque rupture).

In some embodiments, a controller is configured to plot scalar blood flow characteristic values obtained over a time interval for a plurality of adjacent sample volumes. For instance, a controller may be configured to store generated magnitude and/or angle values in data structures that associate each value (or magnitude and angle value pair) with a sample volume index value indicating the location of the sample volume to which the value pertains and a time index value indicating the time to which the value pertains. For a given set sample volume locations and a time interval, the controller may be configured to plot values corresponding to the sample volumes and time interval as points on a graph whose abscissa represents the relative locations of the sample volumes and whose ordinate represents the values.

For example, given a set of velocity magnitude and/or angle records associated with sample volume index values (e.g., cartesian coordinates) and time index values (e.g., timestamps, counter values, memory locations or the like) a controller may be configured to:

obtain a start time index value, an end time index value, a start sample volume index value and an end sample volume index value (e.g., by reading a memory location having a user input values for these values);

ascertain a first plot subset of velocity magnitude and/or angle records to be plotted as the records in the set that are associated with sample volume index values along the line segment extending between the start sample volume index value and the end sample volume index value;

ascertain a second plot subset of velocity magnitude and/or angle records to be plotted as the records in the first plot subset of velocity magnitude and/or angle records that are associated with time index values in the range defined by the start time index value and the end time index value;

determine a number of velocity magnitude and/or angle values to be plotted at each location along the plot abscissa (e.g., by dividing the range of the sample volume indices associated with the records in the second plot subset by the resolution of the plot abscissa);

determine a reference index value (e.g., a sample volume index) corresponding to the start of the abscissa;

transform the sample volume index values associated with the records in the second plot subset into translated sample volume index values that lie along the abscissa (e.g., apply a transformation matrix effective to rotate, translate and scale coordinates on the line segment extending between the start sample volume index value and the end sample volume index value to lie along the abscissa); and for each location along the abscissa, plot the velocity magnitude and/or angle values in the records associated with translated sample volume index values corresponding to the location.

In some embodiments, a controller may be configured to update a plot of velocity magnitude and/or angle values obtained over a moving window time interval for a plurality of adjacent sample volumes. In some such embodiments, the controller may be configured to add records to the first plot subset as the records are generated, and to remove values from the plot when the time index value associated with the value is offset from a current time index value by more than a threshold amount.

In some embodiments, a controller is configured to determine a display attribute for a cursor, or a portion of a cursor, overlaid on a B-mode image corresponding to an indication of a blood velocity characteristic. A controller may be configured to determine a display attribute corresponding to an indication of a blood velocity characteristic using a function, lookup table, logic circuit, or the like. For example, a controller may be configured to determine a color for a portion of a cursor corresponding to particular sample volume, or set of sample volumes, according to the variability of blood flow measurements in the sample volume, or set of sample volumes.

In some embodiments, the duration and/or relative timing between time intervals is user adjustable. In some such embodiments, display 90 comprises a timescale with adjustable markers for setting the start and end points of the time intervals. In some embodiments, the timescale comprises a plot of cardiac and/or respiratory activity, for example, an ECG trace and/or a respiration graph, which may provide information useful in setting the start and end points of time intervals.

Figure 9A:
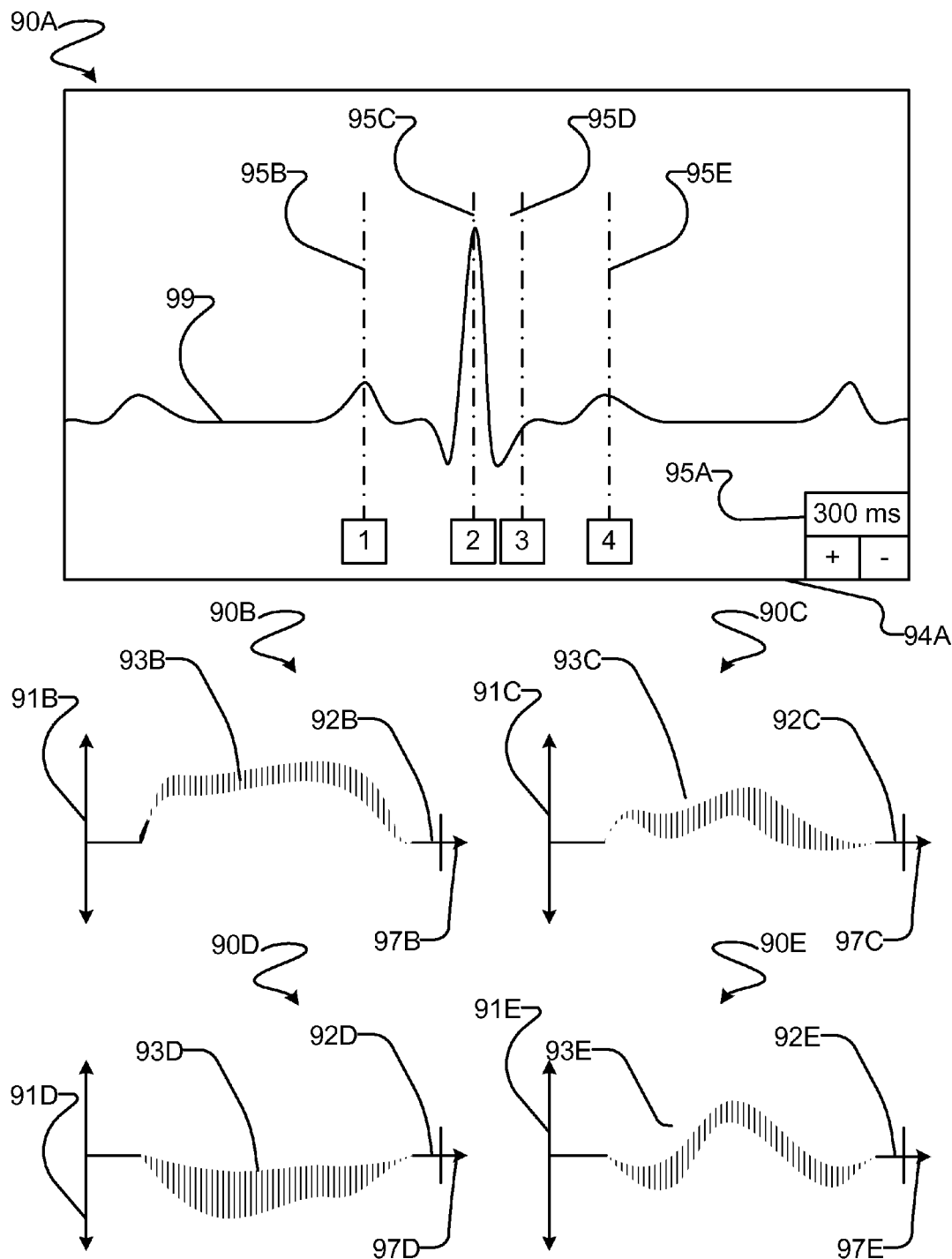

FIG. 9A shows a display 90A comprising a graph 94A and graphs 90B, 90C, 90D and 90E. Graph 94A includes an ECG trace 99, a time interval length control 95A, and user-positionable cursors 95B, 95C, 95D and 95E. In the embodiment illustrated in FIG. 9A, all time intervals of graphs 90B, 90C, 90D and 90E are the same. Control 95A is user-controllable to specify the duration of the time intervals of graphs 90B, 90C, 90D and 90E. Control 95A includes a numerical indication of the duration of the time intervals of graphs 90B, 90C, 90D and 90E.

The positions of cursors 95B, 95C, 95D and 95E indicate the center-points of the time intervals of graphs 90B, 90C, 90D and 90E. Cursors 95B, 95C, 95D and 95E may be positioned by a user along trace 99 at moments in the cardiac cycle corresponding to particular cyclical blood flow characteristics. In alternative embodiments, graph 94A has two cursors for each of graphs 90B, 90C, 90D and 90E, which cursors mark the start and end of the time interval of their respective graphs. In some embodiments, graph 94A has one more cursor than there are time interval graphs of blood flow velocity (i.e., if there are n intervals, graph 94A has n+1 cursors). In such embodiments, a first cursor marks that start of a first time interval, a last cursor marks the end of the last time interval and the other cursors mark the divisions between time intervals, which are continuous.

Features of displays 90 and 90A may be combined with one another and/or with features of other displays described herein. For example, a display may include a B-mode image, an ECG trace and blood velocity magnitude versus position graphs.

In some embodiments, time persistence is applied to one or more velocity magnitude versus position curves. In such embodiments, the shape of the velocity magnitude versus position curve will change over time as new velocity measurements are plotted and old velocity measurements are removed. In some such embodiments the duration of the time persistence window is user adjustable. In the extreme case, the time persistence window may span only a single velocity measurement, in which case the velocity magnitude versus position curve will show the instantaneous velocity magnitude along a line of adjacent sample volumes. In some embodiments, time persistence is augmented using color and/or brightness to indicate the relative age of measurements plotted. In such embodiments, points forming the velocity magnitude versus position curve may appear to change color and/or fade as they age.

Display attributes, such as, for example, color and/or brightness, may also be used to indicate the prevalence of a similar velocity magnitude measurements in a persistence window. Consider for example a blood vessel in which velocity magnitude changes cyclically (e.g., with the cardiac cycle) and is relatively constant for a part of the cycle. Without display attribute augmentation, the period of constant velocity magnitude can only be perceived by observing the velocity magnitude versus position curve over time (i.e., the same value will be added to the plot during the period of constancy). After the period of constant velocity ends, time persistence will preserve for the duration of the persistence window the plot of the velocity magnitude value during the constant period, but it will not be possible for a user to infer how long that value persisted relative to newly plotted velocity magnitude values. In some embodiments, the prevalence of velocity magnitude values in a persistence window is indicated by one or more display attributes (e.g., color, brightness, a combination thereof, or the like). In terms of the constant value example, an example embodiment may have the brightness (and/or color) of the plotted point corresponding to the constant value increasing (and/or changing in some predetermined manner) over the period of constant velocity, and fading (and/or changing in a different predetermined manner) after the period of constant velocity ends.

Different display attributes may be applied to indicate age and prevalence of velocity magnitude values in the time persistence window. For example, color may be used to indicate age and brightness to indicate prevalence, or vice versa. Different display attributes may be applied to indicate combinations of time-varying blood flow characteristics, measurement prevalence and/or measurement age. For example, brightness may be used to indicate relative age of plotted points and color used to indicate velocity magnitude variability.

In some embodiments, a controller is configured to track the number of values corresponding to each plotted point on a plot of velocity magnitude and/or angle values obtained over a time interval for a plurality of adjacent sample volumes. For example, a controller may be configured to maintain a counter for each location on the plot (e.g., for every coordinate in the domain and range of the plot), incrementing each counter when records having values corresponding to the counter join the plotted subset and decrementing each counter when records having values corresponding to the counter are removed from the plotted subset. The controller may configured to determine a display attribute for each plot location according to the value of the location's corresponding counter and to plot a point having the display attribute at the location.

Velocity information may be combined with ultrasound echo strength data to estimate the volume and/or mass of blood flowing through a sample volume. The strength of an ultrasound echo returning from a sample volume is proportional to energy of the transmitted ultrasound pulse and the mass of solids in the sample volume. Where transmitted energy that causes the echo and the relationship between solid mass and volume is known, as for instance between the mass of erythrocytes per unit blood volume, echo strength may be related to volume with precision. Volumetric and/or mass flow in a sample volume vessel may be determined by integrating the velocity information weighted by echo strength and cross-sectional area corresponding to sample volume.

In some embodiments ultrasound data is acquired for a group of adjacent sample volumes that span a blood vessel, and volumetric and/or mass flow across a cross-section of the vessel containing the sample volumes is estimated using a measured or assumed vessel cross-section. A measured vessel cross section may be obtained, for instance, by orienting an ultrasound probe to obtain a B-mode image of the cross-section or by importing vessel cross-section information derived from another imaging modality (e.g., magnetic resonance imaging). In some embodiments, a user who has oriented an ultrasound transducer to obtain a B-mode image of the cross-section of a vessel may trace a contour of the cross-section on a touch-screen image display to determine a vessel cross-section.

Alternatively, a vessel cross-section may be assumed to be a geometric shape (e.g., a circle) or a more complex curve. In some embodiments, a library of vessel cross-sections corresponding to particular blood vessel types and/or blood vessel locations are provided. In such embodiments, a user control is provided for selecting a suitable vessel cross-section. In some embodiments, a user control is provided for specifying the dimensions of an assumed vessel cross section. Users may obtain an understanding of the shape of a blood vessel cross-section by acquiring multiple images of a blood vessel using different probe orientations. Using such an understanding, a user may choose an appropriate vessel cross-section, specify its dimensions.

In some embodiments a user control is provided for specifying a location of a chord, such as a bi-sector, on a measured or assumed vessel cross-section that corresponds to a line of sample volumes for which velocity and echo strength information for determining volumetric and/or mass flow has been acquired. Velocity information obtained for sample volumes corresponding to a bi-sector, or other chord, of a vessel cross-section may be extrapolated radially to span the cross-section. In some embodiments, users may select an extrapolation function from a library of extrapolation functions corresponding to particular blood vessel types and/or blood vessel locations.

In embodiments that provide three-dimensional imaging, the cross-section of a vessel may be determined from images and the determined cross-section used to calculate volumetric and/or mass blood flow.

Figure 10:
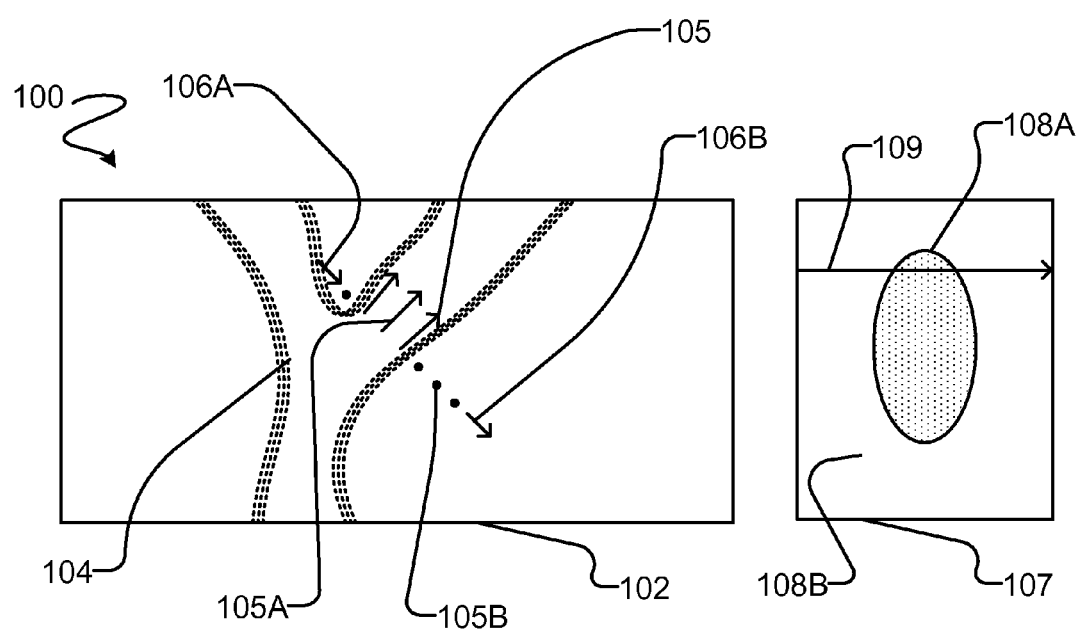
FIG. 10 is a display according to an example embodiment.

FIG. 10 shows a display 100 according to example embodiments. Display 100 comprises a B-mode image 102 of a rectangular area of a plane in a body. Image 102 comprises an outline 104 of a blood vessel. Vector markers 105 indicate the determined velocities along a line defined between cursors 106A and 106B in the plane imaged. Vector markers 105A comprise directional arrows indicating the projection of the true velocity of blood flowing in the blood vessel represented by outline 104 onto the plane of image 102. Vector markers 105B comprise dots, which indicate regions of zero velocity (e.g., stationary tissue).

In embodiments, a controller is configured to determine locations for sample volumes corresponding to a line defined between cursors, such as cursors 106A and 106B. In some embodiments, a controller is configured to generated vector Doppler information for particular sample volumes, such as sample volumes corresponding to a line between cursors like cursors 106A and 106B.

Display 100 also comprises B-mode image 107 of a rectangular area of a plane in the body. The plane of image 107 is perpendicular to plane 102. The horizontal extent of image 107 corresponds to the line between cursors 106A and 106B. The intersection of image 107 with the plane of image 102 is marked by cursor 108. Cursor 108 comprises a directional arrow, whose orientation corresponds to the orientation of cursor 106B on image 102. Image 107 comprises closed FIG. 109A. Closed FIG. 109A corresponds to points in the body imaged that are in the plane of image 107 and have non-zero velocity. Empty space 108B corresponds points in the body imaged that are in the plane of image 107 that have zero velocity. Those skilled in the art will appreciate that closed FIG. 109A corresponds to the cross-section of the blood vessel represented by outline 104 along the line defined by vector markers 105.

The extent of image 107 and its intersection with image 102 may be controlled by gating of received echo samples to acquire echo data from a set of co-planar sample volumes. Some embodiments comprise a method for automatically gating received samples so that image 107 comprises an image of a cross-section of the blood vessel spanned and/or intersected sample volumes corresponding to the line segment connecting cursors 106A and 106B. Where the line segment connecting cursors 106A and 106B corresponds to a set of sample volumes (in the plane of image 102) that comprise sample volumes in a blood vessel, velocity information acquired from the sample volumes in the blood vessel will indicate non-zero velocity.

In embodiments, a controller iteratively adjusts the receive sample gating to acquire velocity information from sample volumes corresponding to projections of the line segment connecting cursors 106A and 106B onto planes that are parallel to and successively more spaced apart from the plane of the image 102. This iterative process may continue until velocity information from sample volumes corresponding to a projection no longer indicate non-zero velocity. Where the sample volumes interrogated are successively further from the initial plane (i.e., the plane of image 102), the first plane for which velocity information indicates entirely zero velocity may be designated as a boundary of a planar region that encloses a blood vessel cross section.

Figure 11:
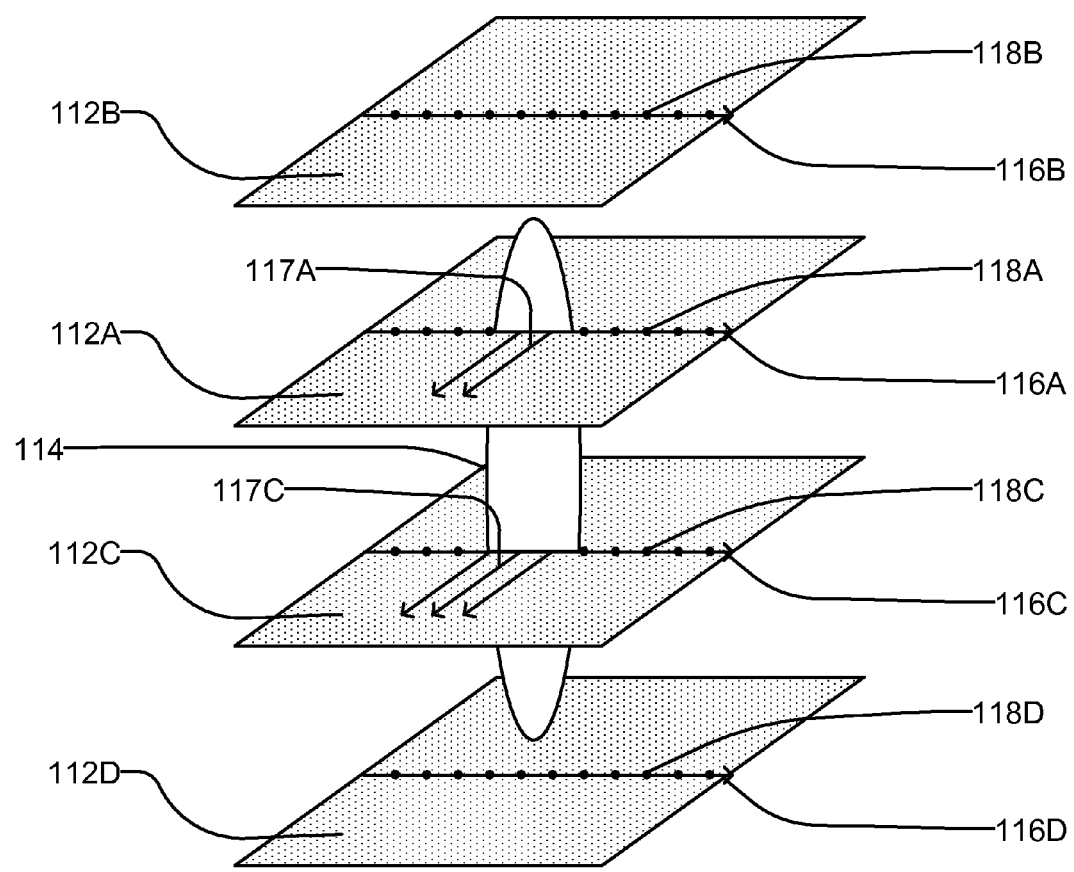
FIG. 11 is a schematic illustration of a method according to an example embodiment.

This process is illustrated schematically in FIG. 11. Plane 112A corresponds to the plane of an image acquired by a user. Plane 112A intersects a blood vessel having a cross section shown by contour 114. Contour 114 lies in a plane that intersects plane 112A at a right angle along line segment 116A. Line segment 116A may correspond to a user-positioned cursor on an image of plane 112A. The measured velocity along the portion of line segment 116A inside contour 114 is non-zero, as indicated by markers 117A. The measured velocity along the portion of line segment 116A outside contour 114 is zero, as indicated by markers 118A.

Plane 112B is parallel to and spaced apart from plane 112A in a first direction. Line segment 116B is a parallel projection of line segment 116A onto plane 112B. The measured velocity at all points on line segment 116B is zero, as indicated by markers 118B. In embodiments, this condition is interpreted as indicating that the blood vessel crossed by line segment 116A does not extend to plane 112B. This information may be used to determine a an extent of an image of a cross-section of a blood vessel in a first direction (e.g., the top of image 107).

Plane 112C is parallel to and spaced apart from plane 112A in a second direction. Line segment 116C is a parallel projection of line segment 116A onto plane 112C. The measured velocity along the portion of line segment 116C inside contour 114 is non-zero, as indicated by markers 117C. The measured velocity along the portion of line segment 116C outside contour 114 is zero, as indicated by markers 118C. In embodiments, this condition is interpreted as indicating that the blood vessel crossed by line segment 116A extends across plane 112C. This information may be used to cause an automated process to obtain velocity information along a projection of line 116A onto another plane parallel to and spaced further from plane 112A in the second direction than plane 112C.

Plane 112D is parallel to and spaced apart from plane 112A in the second direction. The distance between plane 112D and 112A is greater than the distance between plane 112C and 112A. Line segment 116D is a parallel projection of line segment 116A onto plane 112D. The measured velocity at all points on line segment 116D is zero, as indicated by markers 118D. In embodiments, this condition is interpreted as indicating that the blood vessel crossed by line segment 116A does not extend to plane 112D. This information may be used to determine an extent of an image of a cross-section of a blood vessel in the second direction (e.g., the bottom of image 107).

The method of iteratively interrogating sample volumes at greater distances from an image plane to determine the extent of a blood vessel cross-section intersecting the image plane may be modified in various ways. For example, in some embodiments, the velocity information obtained for sample volumes having non-zero velocity may be multiplied by the strength of echoes returned from those sample volumes, and the products summed to determine the volumetric and/or mass flow through the sample volumes. Where the method traverses an vessel cross-section, the volumetric and/or mass flow through the cross-section may be determined in this manner.

In some embodiments, volumetric and/or mass flow in one or more sample volumes and/or across a vessel is determined continually and displayed graphically and/or numerically (e.g., in manners similar to those disclosed herein for the display of other scalar blood flow characteristics). Volumetric flow may be integrated over time to yield a measure of the volume of fluid that has passed through a vessel over time. Embodiments that provide graphs of cardiac and/or respiratory activity may provide user controllable cursors for marking points in the cardiac and/or respiratory cycle to start and end integrals of volumetric and/or mass flow.

Figure 12:
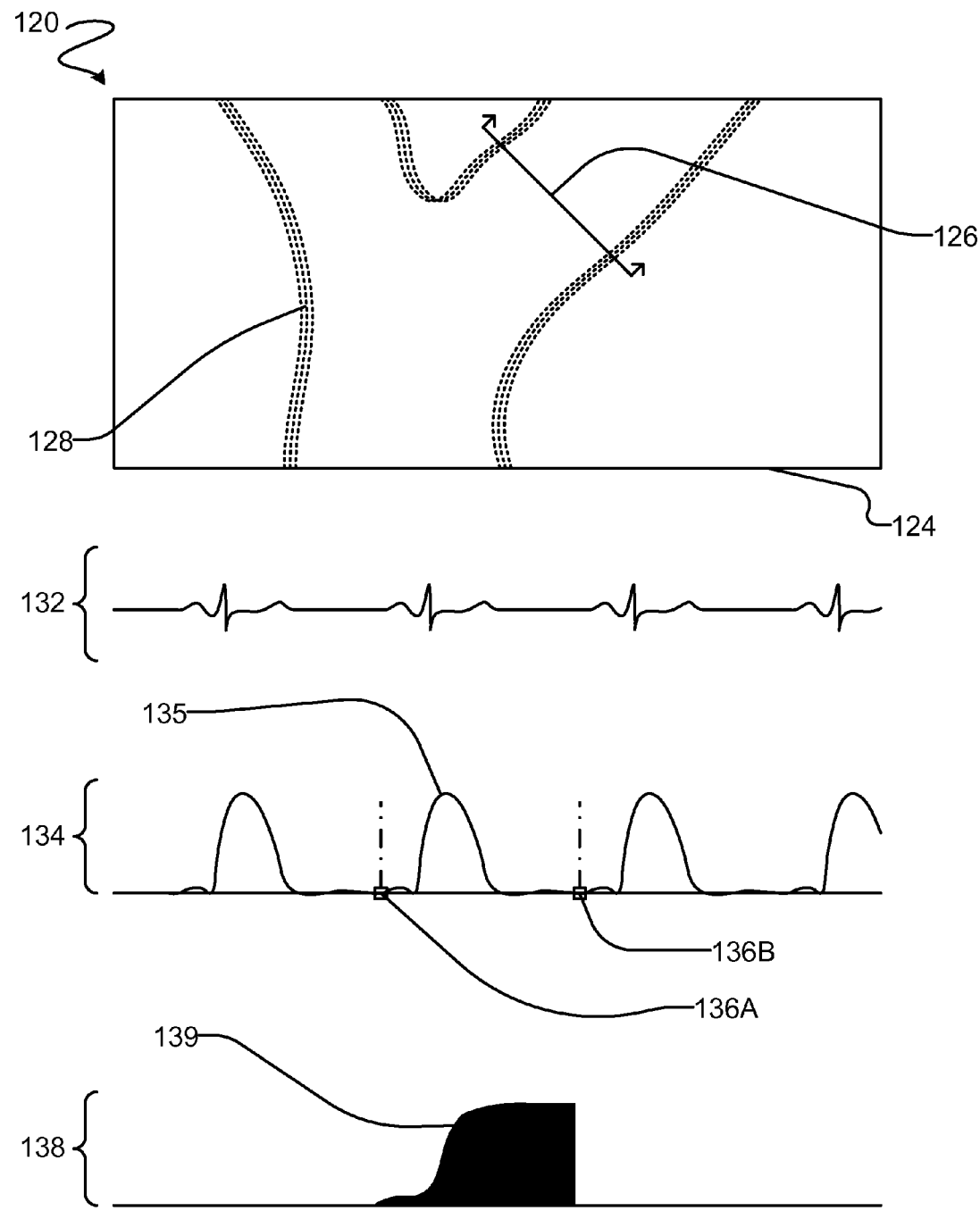
FIG. 12 is a display according to an example embodiment.

FIG. 12 shows schematically a display 120 comprising a B-mode image 124 with a line segment cursor 126 across an outline of a blood vessel 128. In the illustrated embodiment, cursor 126 has arrows to indicate the flow direction that is regarded as positive. Below image 124 is a graph of cardiac activity 132 and a graph 134 of instantaneous volumetric flow in vessel 128 across cursor 126. In graph 134, curve 135 represents the instantaneous volumetric flow in vessel 128 across cursor 126.

Graph 134 also comprises cursors 136A and 136B. Cursors 136A and 136B are user positionable. In the illustrated embodiment, cursors 136A and 136B mark the start and end, respectively, of a time interval over which the instantaneous volumetric flow in vessel 128 across cursor 126 is integrated. Graph 138 is a graph of cumulative volume of blood flow through a cross-section of vessel 128 corresponding to cursor 126. In graph 138, curve 139 represents the volume of blood that has flowed through a cross-section of vessel 128 corresponding to cursor 126 from the time marked by cursor 136A to the time marked by cursor 136B (i.e., cumulative volumetric flow). The volume of blood flow over a time interval marked by cursors 136A and 136B may be used to determine blood scalar flow characteristics for the time interval, such as, for example, cumulative flow volume, mean instantaneous flow rate, or the like.

In some embodiments, display 120 comprises one or more numerical indications of scalar blood flow characteristics at the time(s) indicated by user-positionable cursors on one or more of graphs 132, 134 and 136. Such cursors may be positioned to correspond to peak systolic flow velocity and minimum diastolic blood flow velocity, and numerical values of scalar blood flow characteristics at times corresponding thereto displayed. Cursors may also be used to indicate time intervals on graph 134 over which time-dependent scalar blood flow characteristics may be determined. For example, cursors could be positioned to indicate an interval over which to determine mean instantaneous blood flow rate, the relax time from peak instantaneous blood flow velocity magnitude to minimum instantaneous diastolic blood flow velocity magnitude, points from which to calculate the slope of blood flow velocity magnitude, or the like.

In some embodiments, display 120 comprises a plurality of cursors positionable to indicate multiple blood vessel cross-sections. Some such embodiments comprise a corresponding plurality of graphs and/or numerical displays of instantaneous and/or time-averaged volumetric and/or mass flow and/or cumulative flow volume and/or mass. Such displays may be incorporated into systems for determining complex blood flow conditions, which conditions may have diagnostic value as indicators of physiological characteristics (e.g., the presence of arterial stenosis, blood steals, etc.), susceptibility to disease (e.g., stroke), effectiveness of treatments (e.g., effectiveness of embolization therapy, flow through angioaccess fistulae), or the like. Such systems may be configured to combine data obtained along multiple blood vessel cross-sections to determine the existence of complex blood flow conditions.

Figure 13:
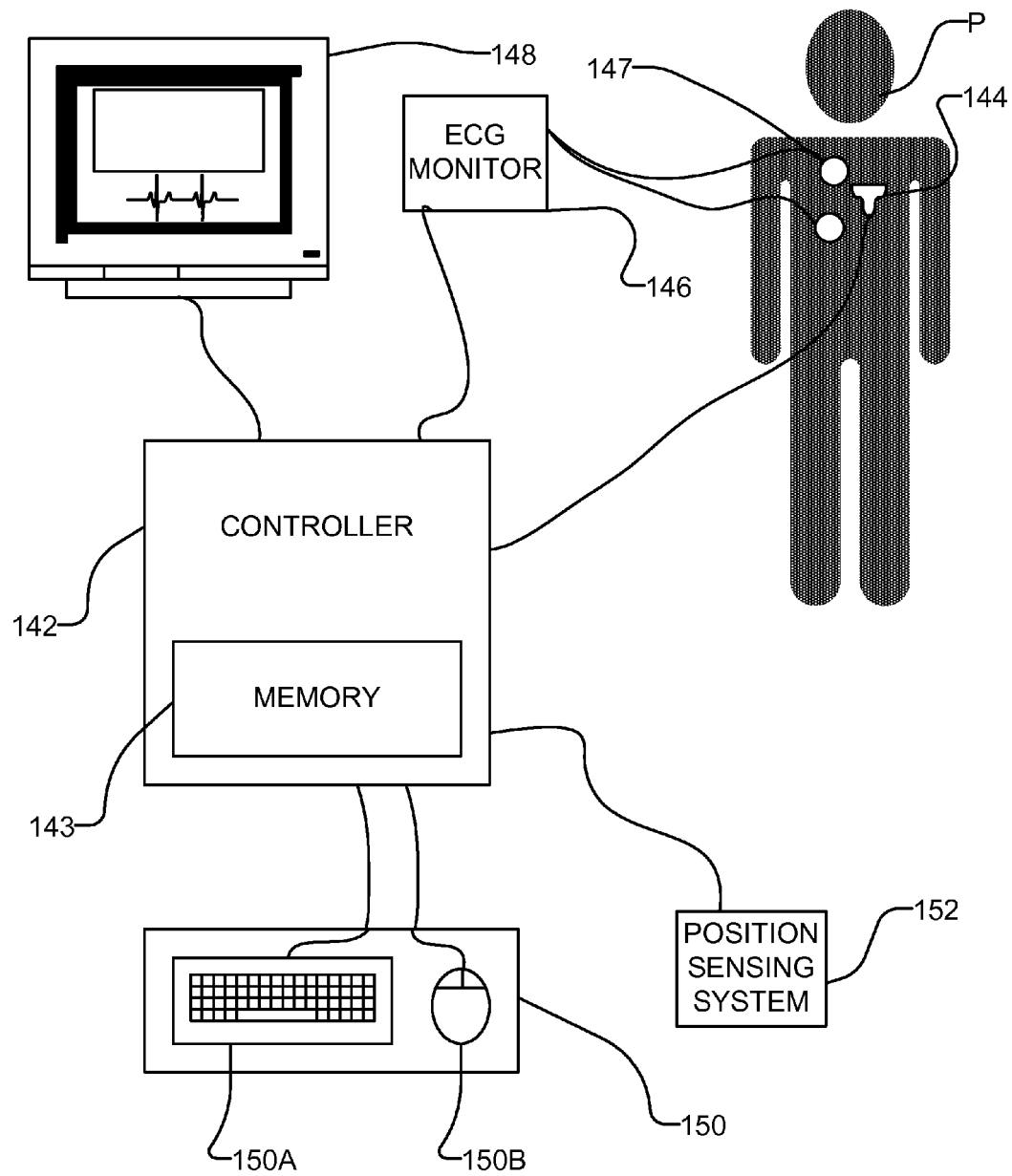
FIG. 13 is a schematic view of a vector Doppler ultrasound system.

FIG. 13 is a schematic illustration of a system 140 that may be used for determining complex blood flow conditions. System 140 comprises a controller 142 connected to an ultrasound transducer 144, an ECG monitor 146, a display 148, and a user input device 150.

Ultrasound transducer 144 acquires ultrasound data representative of ultrasound pulses reflected from structures inside the body of patient P. Controller 142 may be configured to control aspects of the operation of ultrasound transducer 144. For example, controller 142 may control the transmission of pulses from ultrasound transducer 144 and/or the gating of samples of reflected pulses received at ultrasound transducer 144. Ultrasound transducer 144 communicates the ultrasound data it acquires to controller 142.

Controller 142 comprises memory 143. Controller 142 may be configured to store data representative of signals acquired by ultrasound transducer 144 in memory 143. Controller 142 processes ultrasound data provided by ultrasound transducer 144. Controller 142 is configured to process the ultrasound data to generate vector Doppler information and B-mode images. Controller 142 may be configured to store vector Doppler information and/or B-mode image data in memory 143.

Controller 142 is configured to display B-mode images generated from ultrasound data on display 148. Controller 142 is configured to display user-positionable cursors for identifying locations on displayed B-mode images corresponding to sample volumes in the body of patient P at which to determine blood velocity information. For example, controller 142 may be configured to display cursors like cursor 126 in FIG. 12. Controller 142 may be configured to display a plurality of such cursors.

ECG monitor 146 comprises leads 147 operatively coupled to a patient P. Leads 147 provide signals from patient P to ECG monitor 146. ECG monitor 146 processes the signals from patient P to generate a signal indicative of the activity of the heart of patient P. Controller 142 is configured to display on display 148 an ECG trace generated from the signal provided by ECG monitor 146, which is indicative of the activity of the heart of patient P. Controller 142 may be configured to display user-positionable cursors for moments in time along the displayed ECG trace.

Controller 142 is configured to generate and display on display 148 blood flow velocity information for, or relating to, one or more sample volumes in the body of patient P that correspond to the location of user-positionable, sample-volume indicating cursors on display 148. Displayed blood flow velocity information may comprise one or more graphical elements, such as, for example:
  vector markers;
  instantaneous blood flow velocity magnitude vs. position graphs;
  instantaneous blood flow velocity magnitude vs. time graphs;
  instantaneous blood flow velocity angle vs. position graphs;
  instantaneous blood flow velocity angle vs. time graphs;
  instantaneous volumetric flow vs. time graphs;
  instantaneous mass flow vs. time graphs;
  cumulative volumetric flow vs. time graphs;
  cumulative mass flow vs. time graphs;
  first time derivative of instantaneous blood flow velocity magnitude vs. time graphs;
  first time derivative of instantaneous blood flow velocity magnitude vs. position graphs;
  first time derivative of instantaneous blood flow velocity angle vs. time graphs;
  first time derivative of instantaneous blood flow velocity angle vs. position graphs;
  first time derivative of instantaneous volumetric flow vs. time graphs;
  first time derivative of instantaneous mass flow vs. time graphs;
  blood flow velocity magnitude variability (e.g., moving window range, standard deviation, variance, etc.) vs. time graphs;
  blood flow velocity angle variability (e.g., moving window range, standard deviation, variance, etc.) vs. time graphs; and/or
  the like.

Displayed blood flow information may comprise one more numerical elements, such as, for example:
  instantaneous blood flow velocity magnitude;
  instantaneous blood flow velocity angle;
  mean blood flow velocity magnitude;
  mean blood flow velocity angle;
  median blood flow velocity magnitude;
  median blood flow velocity angle;
  blood flow velocity magnitude histograms;
  blood flow velocity angle histograms;
  instantaneous volumetric blood flow;
  instantaneous mass blood flow;
  cumulative volumetric blood flow;

cumulative mass blood flow;
relax time from peak instantaneous blood flow velocity magnitude to minimum instantaneous diastolic blood flow velocity magnitude;
blood flow velocity magnitude variability (e.g., moving window range, standard deviation, variance, etc.);
blood flow velocity angle variability (e.g., moving window range, standard deviation, variance, etc.); and/or
the like.

Input device 150 provides user input to controller 142. In the illustrated embodiment, input device 150 comprises keyboard 150A and computer mouse 150B. Input device 150 may comprise other user interfaces. In some embodiments, display 148 comprises a touch screen element, which may form part of input device 150.

A user may use input device 150 to control aspects of the operation of controller 142. Input device 150 may provide controls for manipulating the locations of user-positionable cursors displayed on display 148. The locations of such cursors on display 148 may be interpreted by controller 142 as specification of the type and characteristics of blood velocity information displayed on display 148. For example, a user may use input device 150 to control the location of user-positionable cursors displayed on display 148. The positions of such cursors may be interpreted by controller 148 as specifying sample volumes in the body of patient P for which to acquire blood velocity information, points in time for which blood velocity information is to be displayed, intervals of time for which blood velocity information is to be displayed, intervals of time over which derivative blood velocity information (e.g., mean blood velocity magnitude, cumulative volumetric blood flow, etc.) is to be determined, timing points and/or periods for cyclic behaviours (e.g., points in and/or periods for cardiac and/or respiratory cycles), or the like.

Input device 150 may provide controls for manipulating B-mode images generated by controller 142. For example, a user may interact with input device 150 to control the gating of samples received at ultrasound transducer 144 and thereby change the B-mode image displayed by controller 142 on display 148. Control may be provided for other aspects of the operation of controller 142 and/or ultrasound transducer 144, such as:
beam-steering of ultrasound emitted by ultrasound transducer 144;
Doppler pulse repetition frequency;
transmit frequency;
receive gate size;
receive gate position;
transmit angle;
receive angle;
etc.

In some embodiments, controller 142 is a configured to provide instructions for using system 140 to determine a complex blood flow condition. Controller 142 may be configured to provide a sequence of instructions. Instructions provided by controller 142 may comprise audible and/or visual instructions, such as instructions displayed on display 148. In some embodiments, controller 142 is configured to accept a user input indicative of the fact that the user has completed an action as instructed by controller 142. In some such embodiments, controller 142 monitors this input, and when a user provides the input indicative of having completed the action instructed by controller, controller 142 may provide a next instruction in a sequence of instructions.

Controller 142 may be configured to provide instructions for acquiring a particular B-mode image using ultrasound transducer 144. For example, controller 142 may be configured to instruct a user to position ultrasound transducer 144 so as to obtain an image of the internal and external carotid arteries. Controller 142 may be configured to instruct a user to position ultrasound transducer 144 at a particular location and orientation with respect to the body of patient P. In embodiments, instructions comprise images and/or videos showing the correct positioning of an ultrasound transducer relative to the body of a patient. Instructions provided by controller 142 may comprise example B-mode images representative of the image the user should acquire when ultrasound transducer 144 is correctly positioned.

In some embodiments, system 140 comprises optional position sensing system 152. Position sensing system 152 senses the location and/or orientation of ultrasound transducer 144 in space by communicating with position markers (not shown) that may be mounted on ultrasound transducer 144. In some embodiments, position sensing system 152 senses the location and/or orientation of particular parts of patient P in space by communicating with position markers (not shown) mounted on patient P. Position sensing system 152 provides information specifying the location and/or orientation of ultrasound transducer 144 and/or particular parts of patient P to controller 142. Controller 142 may be configured to use information provided by position sensing system 152 in generating instructions for user placement of ultrasound transducer 144 at a particular location and orientation with respect to the body of patient P. Where controller 142 is so configured, controller 142 may provide feedback to a user of system 140 attempting to position ultrasound transducer 144.

In some embodiments, controller 142 is configured to provide instructions for locating cursors at particular locations on images that are displayed on display 148. Controller 142 may be configured to instruct users to locate cursors relative to internal bodily structures shown in images on display 148. For example, controller 142 may be configured to provide instructions to position a cursor across a particular artery. Such instructions may include the display of an example image of relevant internal bodily structures with markings that indicate the appropriate cursor locations relative to those structures.

Controller 142 may be configured to compute derivative blood flow information. For example, controller 142 may be configured to compute the sum of the volumetric flow of blood across two or more vessel cross-sections in one or more cardiac cycles. Controller 142 may be configured to compute derivative blood flow information such as:
first time derivative of instantaneous blood flow velocity magnitude;
first time derivative of instantaneous blood flow velocity angle;
first time derivative of instantaneous volumetric flow;
first time derivative of instantaneous mass flow;
blood flow velocity magnitude variability statistics (e.g., moving window range, standard deviation, variance, etc.);
blood flow velocity angle variability statistics (e.g., moving window range, standard deviation, variance, etc.);
mean blood flow velocity magnitude;
mean blood flow velocity angle;
median blood flow velocity magnitude;
median blood flow velocity angle; or
the like.

In some embodiments, a controller is configured to compare blood velocity measurements and/or derivative blood velocity information to thresholds to identify physiological characteristics, blood vessel pathologies, susceptibility to disease, effectiveness of treatments, or the like. For example, a controller may be configured to:
- apply a signal analysis function to signals indicative of cardiac and/or respiratory activity to generate timing information for particular physiological events and/or states (e.g., timing of the post-diastolic phase);
- extract blood flow velocity information from a time-associated list of blood velocity information using timing information generated by the application of a signal analysis function (e.g., blood velocity information for the post-diastolic phase);
- determine derivative blood flow velocity information from the extracted blood flow velocity information (e.g., peak blood velocity magnitude in the post-diastolic phase);
- determine one or more thresholds for the derivative blood velocity information indicative of one or more physiological characteristics, blood vessel pathologies, disease susceptibility metrics, treatment effectiveness metrics, or the like (e.g., a threshold for peak blood velocity magnitude in the post-diastolic phase indicative of stenosis);
- compare the derivative blood flow velocity information with the one or more thresholds; and
- display a conclusion based on the result of the comparison.

In some embodiments, a memory contains a library of thresholds, which are associated with one or more types of blood velocity information and one or more physiological characteristics, blood vessel pathologies, disease susceptibility metrics, treatment effectiveness metrics, or the like. In some embodiments, the selection of a threshold(s) for identifying a particular physiological characteristic, a particular blood vessel pathology, susceptibility to a particular disease, effectiveness of a particular treatment, or the like is user-controllable. For example, some embodiments comprise a controller configured to provide an interface for navigating a library of such thresholds and selecting a threshold from the library.

In a particular example embodiment, controller 142 is configured to determine blood flow conditions that may be indicative of increased stroke risk. In this embodiment, controller 142 is configured to instruct the user to complete the following actions:
- acquire a B-mode image of the internal and external carotid arteries;
- position sample-volume indicating cursors on the B-mode image across the internal and external carotid arteries as depicted in the B-mode image; and
- indicate the period of one or more cardiac cycles by positioning cursors along a timescale of an ECG trace displayed on display 148.

In some embodiments, controller 142 is configured to provide a signal analysis function that automatically determines the period of one or more cardiac cycles by, for example, detecting corresponding points in ECG data, pulse data, vector Doppler data or other data that varies with the cardiac cycle. Controller 142 may optionally be configured to instruct the user to specify a vessel cross-section for the internal and external carotid arteries. In some embodiments, controller 142 automatically determines a vessel cross-section for the internal and external carotid arteries.

In the particular example embodiment, controller 142 is configured accept a user input indicative of the fact that the user has completed the actions as instructed. When a user provides this input, controller 142 is configured to determine the cumulative volumetric flow in each of the internal and external carotid arteries over one or more cardiac cycles. In this embodiment, controller 142 is further configured to compute the sum of the cumulative volumetric flow in the internal and external carotid arteries over the one or more cardiac cycles. Controller 142 then displays the instantaneous volumetric flow in the internal artery and the sum of the cumulative volumetric flow in the internal and external carotid arteries over the one or more cardiac cycles. These displays may be graphical and/or numerical.

A user may interpret the fact of normal volumetric flow (e.g., volumetric flow in a range typical of the particular patient, a member of reference population, etc.) in the internal carotid artery in the presence of an internal carotid artery stenosis as a sign that the patient may not have intracranial collateralization or collateralization from the external carotid artery. This condition may indicate that the patient is at risk of stroke. Where there is normal volumetric flow in the internal carotid artery in the presence of an internal carotid artery stenosis, a user may interpret the fact of normal combined volumetric flow in the internal and external arteries as a sign that the patient has no circle of Willis collateral but is collateralizing via the external carotid. This condition may indicate that the patient is at a risk of stroke.

In some embodiments, the controller is configured to compare the instantaneous volumetric flow and/or combined volumetric flow with threshold values corresponding to boundaries of a normal range. In some such embodiments, the controller is configured to display a graphical, textual or numerical result indicating the result of the comparison(s).

Using displays and graphs in example embodiments disclosed herein to graphically show blood flow velocity information can be more intuitive than conventional PW Doppler blood flow examination displays for reasons, which may include one ore more of the following:
- The display does not need to be not cluttered by a manual angle correction cursor.
- Changes to a true velocity angle with time may be shown. This may provide information that may be used to assess blood flow turbulence.
- Changes to a true velocity magnitude with time may be shown. This may provide information that may be used to diagnose conditions characterized by particular blood flow velocities at certain times (e.g., velocity of blood in the carotid artery at the end of the diastolic phase).
- A sample volume may be moved by re-positioning a cursor on an image while graphical and/or numerical blood velocity magnitude and/or angle information is updated in real-time, which permits intuitive searches for and identification of anomalies in blood flow and blood vessel shape (e.g., stenoses).
- A history of blood flow characteristics, including blood velocity magnitude and angle, instantaneous blood flow and blood flow volume, may be shown developing in real time, permitting the user to recognize patterns of changes in blood flow characteristics.
- Numerical measurements for blood flow characteristics at desired times and/or in desired time intervals may be obtained by positioning cursors to indicate the desired times and/or time intervals.
- Volumetric blood flows in vessels can be determined accurately.

As will be apparent to those skilled in the art in the light of the foregoing disclosure, many alterations and modifications are possible in the practice of this invention without departing from the spirit or scope thereof. For example:
- In embodiments where a cursor is provided to indicate a location in space, a direction, a moment in time or the like, multiple cursors may be provided to indicate a plurality of locations, directions, moments or the like, as the case may be. In embodiments that comprise displays of information corresponding to the position of a cursor (e.g., graphs and numeric values) multiple such displays may be provided to correspond to multiple cursors.

In embodiments where display attributes are be used to indicate graphically the characteristics of velocity measurements, any suitable display attribute may be used, such as, for example, color, brightness, or the like.

Display attributes applied to indicate graphically time varying characteristics of velocity measurements may be applied, mutatis mutandis, to indicate graphically spatially varying characteristics of velocity measurements, and vice versa.

Embodiments described in two-dimensional terms may be extended to apply to three-dimensional vector Doppler data.

Elements described as appearing on different displays may be displayed together on a single display.

Where a component (e.g. a controller, display, device, transducer, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Aspects of the invention may be provided in the form of a program product. The program product may comprise any medium which carries a set of computer-readable information comprising instructions which, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, flash RAM, or the like. The computer-readable information on the program product may optionally be compressed or encrypted.

What is claimed is:

1. A method for displaying blood flow information concerning blood in a vessel, the method comprising:
generating ultrasound signals by using an ultrasound transducer;
producing, in electronic format, an ultrasound image of the vessel from the ultrasound signals, wherein the ultrasound image includes a representation of the vessel;
displaying the ultrasound image via a display device;
constructing and displaying a user-positionable cursor overlaid over a sub-portion of the representation of the vessel in the displayed ultrasound image, wherein the user-positionable cursor identifies a single sub-sample volume of interest in the vessel;
obtaining, with a controller and for each of a plurality of different time intervals, a different true velocity vector of blood passing through the same single sub-sample volume located in the vessel wherein the true velocity vectors are determined from the ultrasound signals;
constructing a plurality of vector-markers, each vector-marker including a graphical indicator that indicates a magnitude and an angle of a different one of the true velocity vectors, wherein each of the graphical indicators includes an arrow with a linear line segment having a first end and a second opposing end and a head disposed at the first end;
displaying, concurrently, the arrows with their second ends at a same spatial point that is located within the same single sub-sample volume, wherein each of the arrows extends from the same point that is located within the same single sub-sample volume, and wherein all of the concurrently displayed plurality of the graphical indicators are concurrently visible.

2. The method according to claim 1 comprising: visually displaying the graphical indicators with time-varying flow characteristics that indicate respective time intervals of the plurality of different time intervals.

3. The method according to claim 1 comprising: receiving a user input indicating a maximum number of the graphical indicators to display at any point in time and displaying no more than the maximum number of the graphical indicators at any point in time.

4. The method according to claim 1 comprising: adding a new graphical indicator generated for a current time interval to the display and removing an existing graphical indicator corresponding to an earlier time interval from the display.

5. The method according to claim 1 wherein concurrently displayed graphical indicators differ in appearance according to a temporal order of their respective time intervals.

6. The method according to claim 5 wherein the concurrently displayed graphical indicators comprise arrows, and respective arrows differ in appearance by at least sizes of heads on the arrows, wherein a first graphical indicator for a first time interval has a first arrow head with a first size and a second graphical indicator for a second time interval has a second arrow head with a second size, the first time interval is earlier than the second time interval, and the first size is smaller than the second size.

7. The method according to claim 5 wherein the concurrently displayed graphical indicators comprise arrows, and respective arrows differ in appearance by at least visible faintness, wherein a first graphical indicator for a first time interval has a first visible faintness and a second graphical indicator for a second time interval has a second visible faintness, the first time interval is earlier than the second time interval, and the first visible faintness is greater than the second visible faintness.

8. The method according to claim 5 comprising changing an appearance of an arrow of a visible displayed graphical indicator each successive time internal.

9. The method according to claim 1 wherein a time separation between the different time intervals is specified by a user.

10. The method according to claim 1 comprising: displaying a scale that associates graphical indicator length with a range of numeric velocity magnitude values.

11. The method according to claim 1 comprising:
for each of the plurality of time intervals: determining a scalar blood flow characteristic value based on the corresponding true velocity vector; and
plotting the scalar blood flow characteristic value on a timescale at a location corresponding to the time interval.

12. The method according to claim 11 wherein the scalar blood flow characteristic comprises velocity angle.

13. The method according to claim 11 wherein the scalar blood flow characteristic comprises velocity magnitude.

14. The method according to claim 13 wherein a plurality of velocity magnitude values corresponding to different time intervals are plotted together at a single location along the timescale.

15. The method according to claim 14 wherein the plurality of velocity magnitude values corresponding to different time intervals are plotted together as a plurality of different points at different locations along a value axis.

16. The method according to claim 14 wherein the plurality of velocity magnitude values comprises a first plurality of velocity magnitude values in a first range and a second plurality of velocity magnitude values in a second range different from the first range, and wherein the first plurality of velocity magnitude values are plotted as a first point defined by the location along the timescale and a first coordinate along the value axis, and the second plurality of velocity magnitude values are plotted as a second point defined by the location along the timescale and a second coordinate along the value axis.

17. The method according to claim 16 wherein the first point has a display attribute corresponding to the number of velocity magnitude values in the first plurality of velocity magnitude values.

18. The method according to claim 17 wherein the display attribute comprises at least one of color and brightness.

19. The method according to claim 6 comprising decreasing the size of the arrow head of the first graphical indicator each successive time internal.

20. The method according to claim 7 comprising increasing the visible faintness the first graphical indicator each successive time internal.

21. The method according to claim 6 wherein the concurrently displayed graphical indicators comprise arrows, and respective arrows differ in appearance by at least faintness, wherein a first graphical indicator for a first time interval has a first faintness and a second graphical indicator for a second time interval has a second faintness, the first time interval is earlier than the second time interval, and the first faintness is greater than the second faintness.

22. The method according to claim 21 comprising decreasing the size of the arrow head of the first graphical indicator each successive time internal.

23. The method according to claim 21 comprising increasing the faintness the first graphical indicator each successive time internal.

24. The method according to claim 21 comprising decreasing the size of the arrow head of the first graphical indicator each successive time internal and increasing the faintness the first graphical indicator each successive time internal.

25. The method according to claim 1, wherein a graphical indicator has at least one of a length, a color or a brightness, and a magnitude of the graphical indicator is indicated by the at least one of the length, the color or the brightness.

26. The method according to claim 1, further comprising: constructing and displaying graphical indications of bisectors of angles between a path from a transmitting transducer element to the sample volume and paths from the sample volume to receive transducer elements.

* * * * *